(12) United States Patent
Ito et al.

(10) Patent No.: US 11,957,796 B2
(45) Date of Patent: Apr. 16, 2024

(54) ISOLATED NANOSHEET AND PRODUCTION METHOD THEREOF

(71) Applicant: THE UNIVERSITY OF TOKYO, Tokyo (JP)

(72) Inventors: Kohzo Ito, Tokyo (JP); Rina Maeda, Tokyo (JP); Shuntaro Uenuma, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 237 days.

(21) Appl. No.: 17/258,953

(22) PCT Filed: Jul. 10, 2019

(86) PCT No.: PCT/JP2019/027255
§ 371 (c)(1),
(2) Date: Jan. 8, 2021

(87) PCT Pub. No.: WO2020/013215
PCT Pub. Date: Jan. 16, 2020

(65) Prior Publication Data
US 2021/0338597 A1    Nov. 4, 2021

(30) Foreign Application Priority Data

Jul. 11, 2018 (JP) ................................ 2018-131589
Apr. 19, 2019 (JP) ................................ 2019-080062

(51) Int. Cl.
*A61K 9/70* (2006.01)
*A61K 31/137* (2006.01)
(Continued)

(52) U.S. Cl.
CPC .......... *A61K 9/7007* (2013.01); *A61K 31/137* (2013.01); *A61K 31/192* (2013.01);
(Continued)

(58) Field of Classification Search
None
See application file for complete search history.

(56) References Cited

U.S. PATENT DOCUMENTS

2009/0213462 A1    8/2009    Wakizaka et al.

FOREIGN PATENT DOCUMENTS

EP          3 243 842          11/2017
JP          2009-204726         9/2009
(Continued)

OTHER PUBLICATIONS

Uenuma, Shuntaro, et al. "Self-assembled Structure of Polyrotaxane Consisting of β-Cyclodextrin and Poly (ethylene oxide)-block-poly (propylene oxide)-block-poly (ethylene oxide) Triblock Copolymer in Bulk System." Chemistry Letters 45.8 (2016): 991-993. (Year: 2016).*
(Continued)

*Primary Examiner* — Jennifer Chin
(74) *Attorney, Agent, or Firm* — Wenderoth, Lind & Ponack, L.L.P.

(57) ABSTRACT

The present invention provides isolated nanosheets each of which includes a plurality of pseudo-polyrotaxanes and which are easily isolated without adhering to each other. The present invention provides an isolated nanosheet including a plurality of pseudo-polyrotaxanes each having one or more first cyclic molecules and a linear molecule included in a cavity or cavities of the first cyclic molecules in a skewered manner, wherein the linear molecules include, as part thereof, first linear molecules each having an ionizable group that ionizes in water or an aqueous solution.

21 Claims, 10 Drawing Sheets

(51) Int. Cl.
| | |
|---|---|
| A61K 31/192 | (2006.01) |
| A61K 31/4704 | (2006.01) |
| A61K 31/5415 | (2006.01) |
| A61K 31/573 | (2006.01) |
| A61K 47/34 | (2017.01) |
| A61K 47/40 | (2006.01) |
| A61K 47/69 | (2017.01) |

(52) U.S. Cl.
CPC ...... *A61K 31/4704* (2013.01); *A61K 31/5415* (2013.01); *A61K 31/573* (2013.01); *A61K 47/34* (2013.01); *A61K 47/40* (2013.01); *A61K 47/6951* (2017.08)

(56) References Cited

FOREIGN PATENT DOCUMENTS

| | | |
|---|---|---|
| JP | 2009-292727 | 12/2009 |
| JP | 2012-155683 | 8/2012 |

OTHER PUBLICATIONS

Silberberg, Malka. "Cyclodextrin as a drug carrier increasing drug solubility." The Science Journal of the Lander College of Arts and Sciences 11.1 (2017): 5. (Year: 2017).*
International Search Report dated Aug. 20, 2019 in International (PCT) Application No. PCT/JP2019/027255.
Maeda et al., "Bioadhesive pseudo-polyrotaxane nanosheet for controlled drug release", Japanese Society for Biomaterials, Proceedings of the 40th Annual Meeting of the Japanese Society for Biomaterials, 2018, p. 253 2E-24, With English translation.
Uenuma et al., "Autonomously isolated pseudo-polyrotaxane nanosheets fabricated via hierarchically ordered supramolecular self-assembly", Chem. Commun., Mar. 1, 2019, vol. 55, pp. 4158-4161.
Rajendiran et al., "Fabrication of 20 nanosheet through self assembly behavior of sulfamethoxypyridazine inclusion complexes with α- and β-cyclodextrins", Spectrochimica Acta Part A: Molecular and Biomolecular Spectroscopy, 2014, vol. 123, pp. 158-166.
Zhang et al., "Mini Review: Nanosheet Technology towards Biomedical Application", Nanomaterials—Basel, 2017, vol. 7, 7 pages.
Tan et al., "Recent Advances in Ultrathin Two-Dimensional Nanomaterials", Chemical Reviews, 2017, vol. 117 pp. 6225-6331.
Li et al., "All Inorganic Halide Perovskites Nanosystem: Synthesis, Structural Features, Optical Properties and Optoelectronic Applications", Small, 2017, vol. 13, 1603996, 24 pages.
Kong et al., "Elemental two-dimensional nanosheets beyond graphene", Chem Soc Rev., 2017, vol. 46, pp. 2127-2157.
Yang et al., "Graphene-like two-dimensional layered nanomaterials: Applications in biosensors and nanomedicine", Nanoscale 2015, vol. 7, pp. 14217-14231.
Okamura et al., "Fragmentation of Poly(lactic acid) Nanosheets and Patchwork Treatment for Burn Wounds", Adv Mater., 2013, vol. 25, pp. 545-551.
Hillmyer et al., "Synthesis and Characterization of Model Polyalkane-Poly(ethylene oxide) Block Copolymers", Macromolecules, 1996, vol. 29, pp. 6994-7002.
Ding et al., "Use of Crown Ether in the Anionic Polymerization of Propylene Oxide-3. Preparation and Micellization of Diblock-Copoly(Oxypropylene/Oxyethylene)", Eur Polym J, 1991, vol. 27, pp. 901-905.
Allegaier et al., "Synthesis of Hydrophobic Poly(alkylene oxide)s and Amphiphilic Poly(alkylene oxide) Block Copolymers", Macromolecules, 2007, vol. 40, pp. 518-525.
Malik et al., "Microwave-assisted polymerization of higher alkylene oxides", Eur Polym J, 2009, vol. 45, pp. 899-910.
Khan et al., "Methods for Selective Modifications of Cyclodextrins", Chem Rev 1998, vol. 98, pp. 1977-1996.
Fujita et al., "Synthesis and characterization of a polyrotaxane consisting of β-cyclodextrins and a poly(ethylene glycol)-poly (propylene glycol) triblock copolymer", Macromol Chem Phys, 1999, vol. 200, pp. 706-713.
Higashi et al., "Effect of guest drug character encapsulated in the cavity and intermolecular spaces of γ-cyclodextrins on the dissolution property of ternary γ-cyclodextrin complex", Int J Pharm, 2017, vol. 531, pp. 543-549.
Higashi et al., "Supramolecular Pharmaceutical Sciences: A Novel Concept Combining Pharmaceutical Sciences and Supramolecular Chemistry with a Focus on Cyclodextrin-Based Supermolecules", Chem Pharm Bull (Tokyo), 2018, vol. 66, pp. 207-216.
Extended European Search Report dated Mar. 29, 2022 in corresponding European Patent Application No. 19833863.4.
Zhang, W. et al., "Tunable Nanosupramolecular Aggregates Mediated by Host-Guest Complexation", Angewandte Chemie, 2016, vol. 128, pp. 11624-11628.
Huang, J. et al., "Soy Protein-Based Nanoconiposites Reinforced by Supramolecular Nanoplatelets Assembled from Pluronic Polymers/ β-Cyclodextrin Pseudopolyrotaxanes", Journal of Applied Polymer Science, 2007, vol. 107, pp. 409-417.
Uenuma et al., "Self-assembled Structure of Polyrotaxane Consisting of β-Cyclodextrin and Poly(ethylene oxide)-block-poly(propylene oxide)-block-poly(ethylene oxide) Triblock Copolymer in Bulk System", Chem. Lett., 2016, 45, 991-993.

* cited by examiner (A)  (B)  (C)

(a)

(b)

(a)          (b)

(a)          (b)

(a)

(b)

ISOLATED NANOSHEET AND PRODUCTION METHOD THEREOF

TECHNICAL FIELD

The present invention relates to an isolated nanosheet including pseudo-polyrotaxanes and/or polyrotaxanes. In particular, the present invention relates to an isolated nanosheet including pseudo-polyrotaxanes and/or polyrotaxanes in which linear molecules forming the pseudo-polyrotaxanes and/or the polyrotaxanes include, as part thereof, first linear molecules each having an ionizable group that ionizes in water or an aqueous solution. The present invention also relates to a material including the isolated nanosheet. The present invention also relates to a production method for the isolated nanosheet.

BACKGROUND ART

In recent years, progress has been made in development of a nanosheet having a thickness of 100 nm or less into applications such as a drug, a catalyst, an optical material, an electrode, and a biomaterial. As a material therefor, there has hitherto been used titanium oxide, boron nitride, carbon nitride, graphene, or the like (see, for example, Non-patent Literatures 1 to 5). However, those inorganic materials, while being liable to have impurities mixed therein, are difficult to purify, and hence have problems with safety for a living body and biocompatibility, posing difficulties in application to drugs and biomaterials.

There are some proposals of methods of synthesizing nanosheets using organic molecules each having biocompatibility.

For example, there may be given a polymer nanosheet formed using polylactic acid (PLA), polydimethylsiloxane (PDMS), or the like.

The polymer nanosheet is obtained by preparing a polymer solution, spin-coating a substrate with the solution, releasing the resultant sheet from the substrate, and pulverizing the resultant released sheet (see, for example, Non-patent Literature 6).

The nanosheets using the organic molecules described above can be expected to be applied to drugs and biomaterials, but have a problem in that their synthesis process and film formation process are complicated, resulting in tremendous cost.

The nanosheets have difficulty in stably existing in a nano-state, and hence have a problem in that the sheets adhere to or aggregate with each other, and also have a problem in that reformation or modification of surfaces thereof for preventing the adhesion or the aggregation is difficult. Accordingly, it is also desired to solve those problems.

CITATION LIST

Non-Patent Literature

NPL 1: Zhang, S.; Sunami et al., Nanomaterials-Basel 2017, 7 (9).
NPL 2: Tan, C. L. et al., Chem Rev 2017, 117 (9), 6225-6331.
NPL 3: Li, X. et al., Small 2017, 13 (5).
NPL 4: Kong, X. K. et al., Chem Soc Rev 2017, 46 (8), 2127-2157.
NPL 5: Yang, G. H. et al., Nanoscale 2015, 7 (34), 14217-14231.
NPL 6: Okamura, Y. et al., Adv Mater 2013, 25 (4), 545-551.

SUMMARY OF INVENTION

Technical Problem

In view of the foregoing, an object of the present invention is to provide a nanosheet which is excellent in safety for a living body and biocompatibility, and hence is applicable to a drug and a biomaterial, and whose synthesis process and film formation process are relatively simple, resulting in a reduction in cost.

Another object of the present invention is to provide, in addition to the above-mentioned object, isolated nanosheets that do not adhere to or aggregate with each other.

Still another object of the present invention is to provide, aside from the above-mentioned object(s) or in addition to the above-mentioned object(s), a material including the above-mentioned nanosheet, in particular, the above-mentioned isolated nanosheets.

Yet another object of the present invention is to provide, aside from the above-mentioned object(s) or in addition to the above-mentioned object(s), a production method for the above-mentioned nanosheet, in particular, the above-mentioned isolated nanosheets.

Solution to Problem

The inventors of the present invention have found the following invention.

<1> An isolated nanosheet including a plurality of pseudo-polyrotaxanes and/or polyrotaxanes each having one or more first cyclic molecules and a linear molecule included in a cavity or cavities of the first cyclic molecules in a skewered manner,
wherein the linear molecules include, as part thereof, first linear molecules each having an ionizable group that ionizes in water or an aqueous solution.

<2> In the above-mentioned item <1>, it is desirable that the first linear molecules each have the ionizable group at or near at least one end thereof, preferably at least one end thereof.

<3> In the above-mentioned item <2>, it is desirable that the first linear molecules each have the ionizable group at or near each of both ends thereof, preferably at each of both ends thereof.

<4> In any one of the above-mentioned items <1> to <3>, it is desirable that the first linear molecules each include at least two moieties.

<5> In the above-mentioned item <4>, it is desirable that the first cyclic molecules includes one of the at least two moieties.

<6> In any one of the above-mentioned items <1> to <5>, it is desirable that the ionizable group be at least one kind selected from the group consisting of a carboxyl group, an amino group, a sulfo group, a phosphoric acid group, a trimethylamine hydrochloride group, a trimethylamine hydrochloride group, a dimethylamino group, a diethylamino group, a methylamino group, an ethylamino group, a pyrrolidine group, a pyrrole group, an ethyleneimine group, a piperidine group, a pyridine group, a pyrylium ion group, a thiopyrylium ion group, a hexamethyleneimine group, an azide group, an imidazole group, a pyrazole group, an oxazole group, a triazole group, an imidazoline group, a morpholine group, a thiazine group, a triazole group, a tetrazole group, a pyridazine group, a pyrimidine group, a pyrazine group, an indole group, a benzimidazole group, a purine group, a benzotriazole group, a quinoline group, a quinazoline group, a quinoxaline group, a pteridine group, a carbazole group, a porphyrin group, a chlorin group, a choline group, an adenine group, a guanine group, a cytosine group, a thymine group, a uracil group, a dissociated thiol group, a dissociated hydroxy group, an azido group, a pyridine group, carbamic acids, guanidines, sulfenic acids, ureas, thioureas, peroxy acids, and analogs and derivatives thereof.

In the case where the first linear molecules each include two or more ionizable groups, such as the case of including ionizable groups at or near one end and at or near the other end, one of the ionizable groups may be identical to or different from the other ionizable group.

It is desirable that the ionizable group be selected from the group consisting of preferably a carboxyl group, an amino group, a sulfo group, a phosphoric acid group, a trimethylamine hydrochloride group, and a dimethylamino group, more preferably a carboxyl group, an amino group, a trimethylamine hydrochloride group, and a dimethylamino group.

<7> In any one of the above-mentioned items <4> to <6>, it is desirable that one of the at least two moieties have a chain length 2 or more times, preferably 7 times, more preferably 14 times as large as the thickness of each of the first cyclic molecules in a central axis direction thereof.

<8> In any one of the above-mentioned items <1> to <7>, it is desirable that the first linear molecules include second linear molecules each having at least three moieties.

<9> In any one of the above-mentioned items <1> to <8>, it is desirable that the linear molecules consist essentially of second linear molecules each having at least three moieties.

<10> In the above-mentioned item <8> or <9>, it is desirable that the second linear molecules be each a block copolymer including at least three blocks.

<11> In the above-mentioned item <10>, it is desirable that the at least three blocks be formed of a moiety formed of polyethylene glycol (PEG) and a moiety formed of polypropylene glycol (PPG).

<12> In any one of the above-mentioned items <1> to <11>, it is desirable that the isolated nanosheet further include a second cyclic molecule free from including any of the linear molecules.

<13> In the above-mentioned item <12>, it is desirable that the second cyclic molecule have a first substance included by a cavity thereof. Examples of the first substance may include, but not limited to, hydrocortisone, phenytoin, naproxen, adenine arabinoside, adenosine, ibuprofen, hydrochlorothiazide, acetylsalicylic acid, methyl salicylate, adamantane, azobenzene, anthracene, pyrene, polyphenylene vinylene, polyaniline, rhodamine, and Nile red.

<14> In any one of the above-mentioned items <1> to <13>, it is desirable that the isolated nanosheet further include a second substance. Examples of the second substance may include, but not limited to: polymers that do not form inclusion complexes with cyclic molecules, such as polystyrene, polyvinylpyridine, polypyridine, polyphenylene, polyacrylamide, polyacrylic acid, polymethacrylic acid, polyvinyl alcohol, polyamide, polyester, polyimide, polybenzoxazole, polyvinyl chloride, polypropylene, polysilane, and polysiloxanes; biopolymers and biomolecules, such as DNA, protein, and polypeptide; inorganic nanomaterials, such as silica nanoparticles, titanium oxide nanoparticles, and silicon nanoparticles; carbon materials, such as fullerene, carbon nanotubes, graphene, graphite, and carbon quantum dots; and metal nanomaterials, such as gold nanoparticles, perovskite quantum dots, CdSeS/ZnS quantum dots, and iron oxide nanoparticles.

<15> In any one of the above-mentioned items <1> to <14>, it is desirable that the first cyclic molecules and the second cyclic molecule be each selected from the group consisting of α-cyclodextrin, β-cyclodextrin, γ-cyclodextrin, a crown ether, a pillararene, a calixarene, a cyclophane, a cucurbituril, and derivatives thereof. Examples of the derivatives may include, but not limited to, methylated α-cyclodextrin, methylated β-cyclodextrin, methylated γ-cyclodextrin, hydroxypropylated α-cyclodextrin, hydroxypropylated β-cyclodextrin, and hydroxypropylated γ-cyclodextrin.

<16> In any one of the above-mentioned items <1> to <15>, it is desirable that the linear molecules be each a copolymer having a configuration represented by: "a moiety formed of PEG-a moiety formed of PPG-a moiety formed of PEG," and the first cyclic molecules be each β-cyclodextrin.

<17> In any one of the above-mentioned items <1> to <16>, it is desirable that the linear molecules be each a triblock copolymer formed only of a configuration represented by: "a moiety formed of PEG-a moiety formed of PPG-a moiety formed of PEG," and the first cyclic molecules be each β-cyclodextrin.

<18> In any one of the above-mentioned items <1> to <17>, it is desirable that the isolated nanosheet have a thickness of from 0.5 nm to 100 nm, preferably from 3 nm to 50 nm, more preferably from 5 nm to 20 nm.

<19> A material including the isolated nanosheet of any one of the above-mentioned items <1> to <18>.

<20> A production method for an isolated nanosheet including a plurality of pseudo-polyrotaxanes each having one or more first cyclic molecules and a linear molecule included in a cavity or cavities of the first cyclic molecules in a skewered manner, the production method including the steps of:
a) preparing the linear molecules;
b) introducing an ionizable group that ionizes in water or an aqueous solution into each of the linear molecules to provide first linear molecules;
c) preparing the first cyclic molecules; and
d) mixing the first linear molecules and the first cyclic molecules in water or an aqueous solution.

<21> In the above-mentioned item <20>, it is desirable that the production method further include, after the step d), e) a step of modifying part of the pseudo-polyrotaxanes of the resultant isolated nanosheet.

<22> In the above-mentioned item <21>, it is desirable that the modifying step be a step of introducing a first substituent at an end of each of the first linear molecules. The first substituent may be a capping group having such a capping action as to prevent dissociation of the first cyclic molecules, may be a group having the action of an ionizable group, or may have any other action.

<23> In the above-mentioned item <22> or <23>, it is desirable that the modifying step be a step of introducing a second substituent into each of the first cyclic molecules.

<24> A production method for an isolated nanosheet including a plurality of pseudo-polyrotaxanes and/or polyrotaxanes each having one or more first cyclic molecules and a linear molecule included in a cavity or cavities of the first cyclic molecules in a skewered manner, the production method including the steps of:
a) preparing the linear molecules;
c) preparing the first cyclic molecules;

d') mixing the linear molecules and the first cyclic molecules in water or an aqueous solution to obtain pseudo-polyrotaxanes and/or polyrotaxanes;

b') introducing an ionizable group that ionizes in water or an aqueous solution into each of the linear molecules of the pseudo-polyrotaxanes and/or the polyrotaxanes obtained in the step d') to provide first linear molecules; and f) mixing the resultant pseudo-polyrotaxanes and/or polyrotaxanes in water or an aqueous solution.

<25> In the above-mentioned item <24>, it is desirable that the production method further include, after the step f), e) a step of modifying part of the pseudo-polyrotaxanes of the resultant isolated nanosheet.

<26> In the above-mentioned item <25>, it is desirable that the modifying step be a step of introducing a first substituent at an end of each of the first linear molecules. The first substituent may be a capping group having such a capping action as to prevent dissociation of the first cyclic molecules, may be a group having the action of an ionizable group, or may have any other action.

<27> In the above-mentioned item <25> or <26>, it is desirable that the modifying step be a step of introducing a second substituent into each of the first cyclic molecules.

<28> A pharmaceutical carrier and/or a pharmaceutical vehicle including the isolated nanosheet of any one of the above-mentioned items <1> to <18>.

<29> A pharmaceutical disintegrant and/or a pharmaceutical binder including the isolated nanosheet of any one of the above-mentioned items <1> to <18>.

<30> In the above-mentioned item <28> to <29>, it is desirable that the isolated sheet be configured to adhere to a target site.

<31> A pharmaceutical including: a pharmaceutically acceptable active ingredient; and the isolated nanosheet of any one of the above-mentioned items <1> to <18>.

<32> A pharmaceutical including: a pharmaceutically acceptable active ingredient; and a pharmaceutical carrier and/or a pharmaceutical vehicle including the isolated nanosheet of any one of the above-mentioned items <1> to <18>.

<33> A pharmaceutical including: a pharmaceutically acceptable active ingredient; and a pharmaceutical disintegrant and/or a pharmaceutical binder including the isolated nanosheet of any one of the above-mentioned items <1> to <18>.

Advantageous Effects of Invention

According to the present invention, the nanosheet which is excellent in safety for a living body and biocompatibility, and hence is applicable to a drug and a biomaterial, and whose synthesis process and film formation process are relatively simple, resulting in a reduction in cost, can be provided.

In addition, according to the present invention, in addition to the above-mentioned effect, the isolated nanosheets that do not adhere to or aggregate with each other can be provided.

Further, according to the present invention, aside from the above-mentioned effect(s) or in addition to the above-mentioned effect(s), the material including the above-mentioned nanosheet, in particular, the above-mentioned isolated nanosheets can be provided.

In addition, according to the present invention, aside from the above-mentioned effect(s) or in addition to the above-mentioned effect(s), the production method for the above-mentioned nanosheet, in particular, the above-mentioned isolated nanosheets can be provided.

BRIEF DESCRIPTION OF DRAWINGS

FIG. 7(A) shows the results of measurement immediately after the preparation of the isolated nanosheets X1, FIG. 7(B) shows the results of measurement after adjustment of a pH to 11, and FIG. 7(C) shows the results of measurement after adjustment of the pH to 7.

FIG. 19(b): after washing).

DESCRIPTION OF EMBODIMENTS

Figure 1:
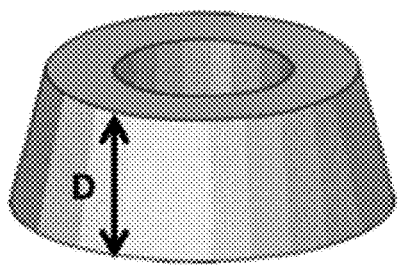
FIG. 1 is a view for schematically illustrating a first cyclic molecule, in which it is illustrated that a distance represented by D is the "thickness of the first cyclic molecule in the central axis direction thereof."

The invention according to the present application is described in detail below.

The present application provides an isolated nanosheet.

The isolated nanosheet of the present invention includes a plurality of pseudo-polyrotaxanes and/or polyrotaxanes each having one or more first cyclic molecules and a linear molecule included in a cavity or cavities of the first cyclic molecules in a skewered manner.

In the present application, "isolated" in the term "isolated nanosheet" means that nanosheets can exist individually without assembling with each other in a solution.

In addition, in the present application, "nano" in the term "isolated nanosheet" refers to having a thickness of 100 nm or less, specifically from 0.5 nm to 100 nm, preferably from 3 nm to 50 nm, more preferably from 5 nm to 20 nm.

In the isolated nanosheet of the present application, it is desirable that the thickness direction thereof be the lengthwise direction of each of the pseudo-polyrotaxanes and/or the polyrotaxanes, in other words, the lengthwise direction of each of the linear molecules. It is desirable that the lengthwise direction of each of the pseudo-polyrotaxanes and/or the polyrotaxanes or the lengthwise direction of each of the linear molecules be the thickness direction of the isolated nanosheet of the present application.

In addition, in the present application, when the term "pseudo-polyrotaxane" is defined as compared to the term "polyrotaxane", while the "polyrotaxane" has, at each of both ends of a linear molecule, a group (capping group) having an action (capping action) that prevents an inclusion cyclic molecule from dissociating from an inclusion state, the "pseudo-polyrotaxane" is defined as being different therefrom in not having such "group (capping group) having a capping action." In short, as used herein, the term "pseudo-polyrotaxane" means one having the group (capping group) having the above-mentioned capping action only at one end of the linear molecule, or having the group (capping group) having the above-mentioned capping action at neither end of the linear molecule.

The linear molecules of the pseudo-polyrotaxanes and/or the polyrotaxanes forming the isolated nanosheet of the present application include, as part thereof, first linear molecules each having an ionizable group that ionizes in water or an aqueous solution.

As described later herein, the ionizable group allows the isolated nanosheet to be formed by virtue of the presence of the ionizable group. Therefore, it is desirable that the linear molecule "have" the ionizable group wherever in the linear molecule the ionizable group is as long as the ionizable group contributes to the formation of the isolated nanosheet.

It is desirable that the first linear molecules each have the ionizable group preferably at or near at least one end thereof, more preferably at least one end thereof, still more preferably at or near each of both ends thereof, most preferably at each of both ends thereof.

In the case of having two or more ionizable groups, such as the case of having ionizable groups at or near both ends, the ionizable groups may be identical to or different from each other. As described later, the first linear molecules may each have, as the ionizable group, a group having a capping action (capping group) by virtue of, for example, the bulkiness of the group.

Pseudo-polyrotaxanes or polyrotaxanes each formed by including the first linear molecule are broadly classified into the following three modes (for the simplicity of description, when an ionizable group is present, description is made on the assumption that the first linear molecule "has" the ionizable group "at or near an end thereof"):

i) a mode in which neither an ionizable group nor a capping group is present at one end of the linear molecule, whereas the linear molecule has an ionizable group at or near the other end (as described later, in some cases, the ionizable group acts as a group having a capping action (capping group) by virtue of, for example, its bulkiness);

ii) a mode in which a capping group is present at or near one end of the linear molecule (the capping group does not have an action as an ionizable group), whereas the linear molecule has an ionizable group at or near the other end (in some cases, the ionizable group acts as a group having a capping action (capping group) by virtue of, for example, its bulkiness); and iii) a mode in which the linear molecule has an ionizable group at or near each of both ends thereof (in some cases, the ionizable group acts as a group having a capping action (capping group) by virtue of, for example, its bulkiness).

The "polyrotaxane" and the "pseudo-polyrotaxane" are defined as described above, and hence, of the modes i) to iii), a case in which the linear molecule has a group having a capping action (capping group) at or near each of both ends thereof means the use of the "polyrotaxane", and a case in which the linear molecule does not have a group having a capping action (capping group) at or near both ends thereof (e.g., the case of the mode i), or a case in which, in the mode ii), the ionizable group is not a group having a capping action (capping group)) means the use of the "pseudo-polyrotaxane".

That the isolated nanosheet of the present invention "includes a plurality" of "pseudo-polyrotaxanes and/or polyrotaxanes" means the case of "including a plurality" of only the "pseudo-polyrotaxanes", the case of "including a plurality" of only the "polyrotaxanes", or the case of "including" a "plurality" of the "pseudo-polyrotaxane(s)" and the "polyrotaxane(s)" in total, including at least one "pseudo-polyrotaxane" and at least one "polyrotaxane".

The isolated nanosheet of the present application may include the following as long as the isolated nanosheet can be formed: a component other than the above-mentioned "pseudo-polyrotaxanes and/or polyrotaxanes", including a second substance to be described later, that is, a component other than the "pseudo-polyrotaxanes and/or polyrotaxanes in which the linear molecules include, as part thereof, first linear molecules each having an ionizable group that ionizes in water or an aqueous solution", in other words, "specific pseudo-polyrotaxanes and/or specific polyrotaxanes". Examples of such component other than the "specific pseudo-polyrotaxanes and/or specific polyrotaxanes" may include, but not limited to, a pseudo-polyrotaxane that is not "specific", and a polyrotaxane that is not "specific".

In short, the isolated nanosheet of the present application may include the following as long as the isolated nanosheet can be formed: a linear molecule other than the first linear molecules; a pseudo-polyrotaxane including a linear molecule other than the first linear molecules as a constituent element; and/or a polyrotaxane including a linear molecule other than the first linear molecules as a constituent element.

It is desirable as described above that each of the first linear molecules "has" the ionizable group. For example, the ionizable group may be directly bonded to "at least two moieties" described later, or may be indirectly bonded the "at least two moieties" via a spacer.

The isolated nanosheets of the present application can be "isolated" without adhering to or aggregating with each other because the linear molecules of the pseudo-polyrotaxanes and/or the polyrotaxanes have the ionizable group.

It is desirable that the first linear molecules each include at least two moieties.

In the present application, the linear molecules and the first cyclic molecules are not particularly limited as long as the molecules can assume a form in which the linear molecule(s) is included in cavities of the first cyclic molecules in a skewered manner.

It is desirable that the first linear molecules each including at least two moieties include second linear molecules each having at least three moieties. In particular, it is preferred that the linear molecules consist essentially of second linear molecules each having at least three moieties, and it is more preferred that the linear molecules consist only of second linear molecules each having at least three moieties.

It is desirable that the second linear molecules each having at least two moieties be each a block copolymer including at least two blocks.

In addition, it is desirable that the second linear molecules each having at least three moieties be each a block copolymer including at least three blocks.

Each block of the "block copolymer" is preferably formed only of one repeating unit, but may have a first spacer group between one repeating unit and the next repeating unit.

In addition, the "block copolymer" may have, between adjacent blocks thereof, a second spacer group, which may be identical to or different from the first spacer group.

Examples of the first spacer group and/or the second spacer group may include, but not limited to: a linear or branched alkykene group having 1 to 20 carbon atoms, such as a methylene group, an ethylene group, a propylene group, a butylene group, or a phenylene group (part of which may be substituted with an aromatic ring, such as a phenyl group); ethers of linear or branched chains each having 1 to 20 carbon atoms; esters of linear or branched chains each having 1 to 20 carbon atoms; and an aromatic group having 6 to 24 carbon atoms, such as a phenyl group.

It is desirable that the first linear molecule is included by the first cyclic molecules, and it is preferred that one of the at least two moieties of the first linear molecules each including the at least two moieties is included by the first cyclic molecule(s). When the first linear molecules each including the at least two moieties include the second linear molecules each having at least three moieties, consist essentially of the second linear molecules, or consist only of the second linear molecules, it is desirable that one of the at least three moieties of the second linear molecules is included by the first cyclic molecule(s). When the linear molecules, and/or the first and/or second linear molecules are each a block copolymer, it is desirable that a "block" is included by the first cyclic molecules.

It is preferable that the moiety at which the linear molecule is included by the first cyclic molecule, that is, one of the at least two moieties of the first linear molecules, one of the at least three moieties of the second linear molecules, or one "block" of the block copolymer have a chain length larger than the thickness of the first cyclic molecule. Herein, the thickness of the first cyclic molecule is more precisely the thickness of the first cyclic molecule in the central axis direction thereof. Now, the "thickness of the first cyclic molecule in the central axis direction thereof" is described with reference to the drawings. FIG. 1 is a view for schematically illustrating the first cyclic molecule. In FIG. 1, a distance represented by D is the "thickness of the first cyclic molecule in the central axis direction thereof."

It is desirable that the moiety at which the first cyclic molecule is included by the linear molecule, that is, one of the at least two moieties of the first linear molecules, one of the at least three moieties of the second linear molecules, and/or one "block" of the block copolymer have a chain length two or more times, preferably five times, more preferably 14 times as large as the thickness of the first cyclic molecule in the central axis direction thereof.

In the present application, as described above, the linear molecule is not particularly limited as long as the linear molecule can assume a form in which the linear molecule is included in cavities of the first cyclic molecules in a skewered manner.

The linear molecule, preferably as a skeleton forming at least two or at least three moieties of the first linear molecule, is desirably selected from the group consisting of polyvinyl alcohol, polyvinylpyrrolidone, poly(meth)acrylic acid, a cellulose-based resin (e.g., carboxymethylcellulose, hydroxyethylcellulose, or hydroxypropylcellulose), polyacrylamide, polyethylene oxide, polyethylene glycol, polypropylene glycol, polyglycerin and derivatives thereof, a polyvinyl acetal-based resin, polyvinyl methyl ether, polyamine, polyethylenimine, casein, gelatin, starch and/or copolymers thereof, a polyolefin-based resin, such as polyethylene, polypropylene, or a copolymer resin with any other olefin-based monomer, a polyester resin, a polyvinyl chloride resin, a polystyrene-based resin, such as polystyrene or an acrylonitrile-styrene copolymer resin, an acrylic resin, such as polymethyl methacrylate, a (meth)acrylic acid ester copolymer, or an acrylonitrile-methyl acrylate copolymer resin, a polycarbonate resin, a polyurethane resin, a vinyl chloride-vinyl acetate copolymer resin, a polyvinyl butyral resin, and derivatives or modified products thereof, polyisobutylene, polytetrahydrofuran, polyaniline, an acrylonitrile-butadiene-styrene copolymer (ABS resin), polyamides, such as nylon, polyimides, polydienes, such as polyisoprene and polybutadiene, polysiloxanes, such as polydimethylsiloxane, polysulfones, polyimines, polyacetic anhydrides, polyureas, polysulfides, polyphosphazenes, polyketones, polyphenylenes, polyhaloolefins, and derivatives thereof. For example, the linear molecule is desirably selected from the group consisting of polyethylene glycol, polyisoprene, polyisobutylene, polybutadiene, polypropylene glycol, polytetrahydrofuran, polydimethylsiloxane, polyethylene, polypropylene, polyvinyl alcohol, and polyvinyl methyl ether. In particular, the linear molecule is desirably polyethylene glycol or polypropylene glycol.

The linear molecules preferably have at least two or at least three moieties. It is desirable that the weight average molecular weight of the linear molecules themselves be from 500 to 500,000, preferably from 1,000 to 20,000, more preferably from 6,000 to 16,000. The weight average molecular weight of the linear molecules may be measured by gel permeation chromatography (GPC). Although measurement conditions for GPC depend on the kinds of the linear molecules, it is desirable that the kinds of eluent and column, a temperature, a standard substance, and a flow rate be appropriately selected.

In addition, the linear molecules are preferably water-soluble linear molecules. The water-soluble linear molecule is not particularly limited as long as the molecule has water solubility, for example, a characteristic that allows 1 g thereof to be dissolved in 1 L of water.

Examples of the skeleton forming at least two or at least three moieties of the water-soluble linear molecule may include, but not limited to, polyethylene glycol, polypropylene glycol, polyvinyl alcohol, polyethylenimine, polyacrylic acid, polymethacrylic acid, polyacrylamide, pullulan, water-soluble cellulose derivatives, such as hydroxypropylcellulose, polyvinylpyrrolidone, polypeptide, and copolymers each including polyethylene glycol.

That is, it is desirable that the water-soluble linear molecule be at least one kind selected from the group consisting of the polymers listed above, preferably at least one kind selected from the group consisting of polyethylene glycol, polypropylene glycol, polyvinyl alcohol, polyethylenimine, and copolymers including polyethylene glycol, more preferably at least one kind selected from the group consisting of polyethylene glycol and polypropylene glycol.

The molecular weight of the water-soluble linear molecule (number average molecular weight or weight average molecular weight) is not particularly limited, but it is desirable that the molecular weight be from 500 to 500,000, preferably from 1,000 to 50,000, more preferably from 2,000 to 20,000.

As described above, part of the linear molecules, the first linear molecules, and/or the second linear molecules of the present invention have an ionizable group that ionizes in water or an aqueous solution. It is desirable that the first linear molecules each have the ionizable group preferably at or near at least one end thereof, more preferably at least one end thereof, still more preferably at or near each of both ends thereof, most preferably at each of both ends thereof.

In the case of having two or more ionizable groups, such as the case of having ionizable groups at or near both ends, the ionizable groups may be identical to or different from each other.

It is desirable that the ionizable group be at least one kind selected from the group consisting of a carboxyl group, an amino group, a sulfo group, a phosphoric acid group, a trimethylamine hydrochloride group, a trimethylamine hydrochloride group, a dimethylamino group, a diethylamino group, a methylamino group, an ethylamino group, a pyrrolidine group, a pyrrole group, an ethyleneimine group, a piperidine group, a pyridine group, a pyrylium ion group, a thiopyrylium ion group, a hexamethyleneimine group, an azide group, an imidazole group, a pyrazole group, an oxazole group, a triazole group, an imidazoline group, a morpholine group, a thiazine group, a triazole group, a tetrazole group, a pyridazine group, a pyrimidine group, a pyrazine group, an indole group, a benzimidazole group, a purine group, a benzotriazole group, a quinoline group, a quinazoline group, a quinoxaline group, a pteridine group, a carbazole group, a porphyrin group, a chlorin group, a choline group, an adenine group, a guanine group, a cytosine group, a thymine group, a uracil group, a dissociated thiol group, a dissociated hydroxy group, an azido group, a pyridine group, carbamic acids, guanidines, sulfenic acids, ureas, thioureas, peroxy acids, and analogs and derivatives thereof. In the case of including ionizable groups at both ends, one of the ionizable groups may be identical to or different from the other ionizable group. As described above, the ionizable group may be arranged so that the first linear molecules may each "have" the ionizable group via a spacer.

It is desirable that the ionizable group be selected from the group consisting of preferably a carboxyl group, an amino group, a sulfo group, a phosphoric acid group, a trimethylamine hydrochloride group, and a dimethylamino group, more preferably a carboxyl group, an amino group, a trimethylamine hydrochloride group, and a dimethylamino group.

In the present application, the first cyclic molecules are molecules that can assume a form in which the linear molecule(s) is included in the cavity of each of the first cyclic molecules in a skewered manner, and are not particularly limited as long as the first cyclic molecules can each assume, as described above, a foam of including one of the first linear molecules, preferably a form of including one of the at least two moieties of the first linear molecules, one of the at least three moieties of the second linear molecules, or one "block" of the block copolymer.

Examples of the first cyclic molecule may include, but are not limited to, α-cyclodextrin ("cyclodextrin" is hereinafter sometimes referred to simply as "CD"), β-cyclodextrin, γ-cyclodextrin, a crown ether, a pillararene, a calixarene, a cyclophane, a cucurbituril, and derivatives thereof. Examples of the derivatives may include, but not limited to, methylated α-cyclodextrin, methylated β-cyclodextrin, methylated γ-cyclodextrin, hydroxypropylated α-cyclodextrin, hydroxypropylated β-cyclodextrin, and hydroxypropylated γ-cyclodextrin.

Inclusion Ratio

As used in the present application, the term "inclusion ratio" refers to the ratio of the cyclic molecules contained in the pseudo-polyrotaxanes and/or polyrotaxanes.

In addition, the term "specified inclusion ratio" refers to an inclusion ratio arithmetically specified from the linear molecules and the first cyclic molecules used for the pseudo-polyrotaxanes and/or the polyrotaxanes, and is specifically specified from the length of each of the above-mentioned linear molecules and the thickness of each of the above-mentioned first cyclic molecules.

The specified inclusion ratio is specifically described.

A case in which polyethylene glycol is used as the water-soluble linear molecule and α-CD is used as the cyclic molecule is considered.

It is known from molecular model calculation that two repeating units of polyethylene glycol are equal to α-CD in thickness. Therefore, a case in which the ratio between the number of moles of α-CD and the number of repeating units is 1:2 is defined as corresponding to a specified inclusion ratio of 100%.

The ratio of the cyclic molecules contained in obtained pseudo-polyrotaxanes and/or polyrotaxanes, that is, the inclusion ratio may be determined by small-angle X-ray scattering (SAXS) measurement of an obtained nanosheet dispersion.

Specifically, the inclusion ratio may be determined from the ratio between: the thickness of the sheet determined by fitting a one-dimensional SAXS profile of an obtained dispersion of pseudo-polyrotaxanes and/or polyrotaxanes through use of a formula assuming a sheet-like structure; and the fully stretched trans chain length of the linear molecule.

Thus, the inclusion ratio of the pseudo-polyrotaxanes and/or the polyrotaxanes may be determined.

In the present application, it is desirable that the inclusion ratio of the pseudo-polyrotaxanes and/or the polyrotaxanes be from 1% to 100%, preferably from 5% to 100%, more preferably from 10% to 100%, most preferably from 20% to 100% when the specified inclusion ratio is set to 100%.

In the present application, it is desirable that the linear molecules be each a copolymer having a configuration represented by: "a moiety formed of PEG-a moiety formed of PPG-a moiety formed of PEG," and the first cyclic molecules be each β-cyclodextrin or γ-cyclodextrin, preferably β-cyclodextrin.

In addition, in the present application, it is desirable that the linear molecules be each a triblock copolymer formed only of a configuration represented by: "a moiety formed of PEG-a moiety formed of PPG-a moiety formed of PEG," an end ionizable group be a carboxylic acid group or an amino group, and the first cyclic molecules be each β-cyclodextrin or γ-cyclodextrin, preferably β-cyclodextrin.

Further, in the present application, it is desirable that the linear molecules be each a polymer formed only of a configuration represented by: "a moiety formed of PEG," an end ionizable group be a carboxylic acid group or an amino group, and the first cyclic molecules be each α-cyclodextrin.

The isolated nanosheet of the present invention may include a component other than the above-mentioned pseudo-polyrotaxanes and/or polyrotaxanes as long as a configuration as an isolated nanosheet can be maintained.

Examples of such component may include, but not limited to: a second cyclic molecule, which may be identical to or different from the first cyclic molecules; a first substance, which may be included in a cavity of the second cyclic molecule; a second substance, which may be identical to or different from the first substance; and a pseudo-polyrotaxane and/or a polyrotaxane other than the "specific" pseudo-polyrotaxanes and/or polyrotaxanes of the present invention.

Examples of the second cyclic molecule may include, but not limited to, cyclic molecules given as examples of the first cyclic molecule.

Although the first substance and the second substance depend on the fields in which the isolated nanosheet of the present invention is used or applied, examples of the first substance may include, but not limited to, hydrocortisone, phenytoin, naproxen, adenine arabinoside, adenosine, ibuprofen, hydrochlorothiazide, acetylsalicylic acid, methyl salicylate, adamantane, azobenzene, anthracene, pyrene, polyphenylene vinylene, polyaniline, rhodamine, Nile red, ethenzamide, prednisolone acetate, rebamipide, salbutamol or salbutamol sulfate, flurbiprofen, beclomethasone, piroxicam, ketoprofen, Timoptol, dorzolamide, dorzolamide hydrochloride, isopropyl unoprostone, diphenhydramine, diphenhydramine hydrochloride, hydroxyzine, hydroxyzine hydrochloride, cetirizine, cetirizine hydrochloride, chlorpheniramine maleate, epinastine hydrochloride, epinastine, levocabastine hydrochloride, levocabastine, levofloxacin, latanoprost, bimatoprost, tafluprost, timolol maleate, basic fibroblast growth factor (bFGF), carboplatin, cisplatin, tegafur, docetaxel, nedaplatin, paclitaxel, pirarubicin, fluorouracil, bleomycin, mitomycin, salicylic acid, flurbiprofen, dexamethasone, amphotericin, piroxicam, pancratistatin, phenytoin, adenine arabinoside, adenosine, diazepam, hydrochlorothiazide, daunorubicin, astemizole, beclomethasone, beclomethasone dihydrochloride, beclomethasone, betamethasone, bendazac, bromazepam, celecoxib, chlordiazepoxide, clobazam, clonazepam, coenzyme Q10, cortisone, curcumin, cyproterone acetate, fluocinolone acetate, flurazepam, flutamide, indomethacin, ketotifen, loratadine, lorazepam, medazepam, meloxicam, natamycin, nimesulide, nimetazepam, nitrazepam, nystatin, prednisolone, progesterone, risperidone, salbutamol, sildenafil, telmisartan, testosterone, triamcinolone, felbinac, suprarenal extract/heparinoid, loxoprofen sodium hydrate, diclofenac sodium, ketoprofen, prednisolone acetate, fluocinolone, loteprednol, difluprednate, triamcinolone, rimexolone, dexamethasone, fluorometholone, metasulfobenzoate sodium, betamethasone sodium phosphate, dexamethasone sodium phosphate, cefmenoxime hydrochloride, ofloxacin, and chloramphenicol. As used herein, the term "first substance" and the teen "second substance" are defined as follows: the "first substance" refers to a substance a part of which is at least partially included by the second cyclic molecule, and the "second substance", unlike the "first substance", refers to a substance that is not in an inclusion state with the second cyclic molecule. In some cases, the same substance is present in the isolated nanosheet in a state of being included by the second cyclic molecule and without being included. In those cases, the substance is present in the isolated nanosheet as each of the "first substance" and the "second substance".

In addition, examples of the second substance may include, but not limited to: polymer materials that do not form inclusion complexes with cyclic molecules, such as polystyrene, polyvinylpyridine, polypyridine, polyphenylene, polyacrylamide, polyacrylic acid, polymethacrylic acid, polyvinyl alcohol, polyamide, polyester, polyimide, polybenzoxazole, polyvinyl chloride, polypropylene, polysilane, and polysiloxanes; biopolymers and biomolecules, such as DNA, protein, and polypeptide; inorganic nanomaterials, such as silica nanoparticles, titanium oxide nanoparticles, and silicon nanoparticles; carbon materials, such as fullerene, carbon nanotubes, graphene, graphite, and carbon quantum dots; and metal nanomaterials, such as gold nanoparticles, perovskite quantum dots, CdSeS/ZnS quantum dots, and iron oxide nanoparticles. The examples of the second substance may also include, but not limited to, Timoptol, dorzolamide, dorzolamide hydrochloride, isopropyl unoprostone, rebamipide, levofloxacin, latanoprost, bimatoprost, tafluprost, timolol maleate, basic fibroblast growth factor (bFGF), cetuximab, docetaxel, nedaplatin, paclitaxel, nedaplatin, paclitaxel, fluorouracil, bleomycin, and mitomycin.

In addition, the isolated nanosheet of the present invention can be formed from molecules that are highly safe for a living body and has high biocompatibility, such as cyclodextrin and polyethylene glycol, and hence is suited for utilization in a living body.

The isolated nanosheet of the present invention may be used for, for example, a material for drug delivery (e.g., a vehicle for drug delivery), bioimaging, a surface modifier, an adhesive, or a wound site adhesion-preventing agent, but is not limited thereto.

In addition, the present invention also provides a material including the above-mentioned isolated nanosheet.

Examples of the material, though depending on fields in which the isolated nanosheet of the present invention is used or applied, may include, but not limited to, a structural material, an artificial prosthetic material, a packaging material, a rubber material, a coating material, a paint, and an adhesive.

As described above, the isolated nanosheet of the present invention may be used as a pharmaceutical carrier and/or a pharmaceutical vehicle including a material for drug delivery (e.g., a vehicle for drug delivery).

In addition, in some aspects, the isolated nanosheet of the present invention may be used as a pharmaceutical disintegrant and/or a pharmaceutical binder. For example, the isolated nanosheet of the present invention can have an action of binding an active ingredient of a pharmaceutical and a component thereof other than the active ingredient, and hence can be used as a pharmaceutical binder. In addition, the isolated nanosheet of the present invention having inside itself the active ingredient of the pharmaceutical can disintegrate into its constituent components, i.e., the linear molecules, the cyclic molecules, and the like depending on the concentration of an aqueous solution, the temperature thereof, the pH thereof, humidity, a time course, and the like, and hence can be used as a pharmaceutical disintegrant.

It is desirable that the isolated sheet of the present invention adhere to target sites including parts of a living body, such as target cells, skin, hair, a tooth, and a bone, medical devices, such as contact lenses, cloth, an interior material for a room, and the like, and it is desirable that the active ingredient be released from the isolated nanosheet after the adhesion. For example, it is desirable that the isolated nanosheet disintegrate to release the active ingredient that the isolated nanosheet has inside itself.

Therefore, the isolated nanosheet of the present invention may be used as a pharmaceutical, specifically a pharmaceutical including a pharmaceutically acceptable active ingredient and the isolated nanosheet of the present invention.

The pharmaceutically acceptable active ingredient is not particularly limited as long as the isolated nanosheet of the present invention can have inside itself the pharmaceutically acceptable active ingredient. Examples of the pharmaceutically acceptable active ingredient may include, but not limited to, naproxen, prednisolone acetate, rebamipide, salbutamol or salbutamol sulfate, flurbiprofen, beclomethasone, piroxicam, and ketoprofen.

The present invention provides production methods I and II for the above-mentioned isolated nanosheets.

Production Method I

In the present application, the production method I can provide an isolated nanosheet including a plurality of pseudo-polyrotaxanes each having one or more first cyclic molecules and a linear molecule included in a cavity or cavities of the first cyclic molecules in a skewered manner, the production method I including the steps of:
a) preparing the linear molecules;
b) introducing an ionizable group that ionizes in water or an aqueous solution into each of the linear molecules to provide first linear molecules;
c) preparing the first cyclic molecules; and
d) mixing the first linear molecules and the first cyclic molecules in water or an aqueous solution.

The "first linear molecules", the "ionizable group", and the "first cyclic molecules" are as described above. For example, as described above, the "first linear molecules" may each "include at least two moieties", and "second linear molecules each including at least three moieties" or the like may be used.

Step a)

The step a) is a step of preparing the linear molecules. The linear molecules may be purchased on the market, or may be produced. As described above, "linear molecules" "each including at least two moieties" may be used. When "linear molecules" "each including at least two moieties" are to be prepared, the linear molecules may be obtained by a method described in, for example, any one of the following Documents 1 to 4.

Document 1: Hillmyer, M. A. et al., Macromolecules 1996, 29 (22), 6994-7002.

Document 2: Ding, J. F. et al., Eur Polym J 1991, 27 (9), 901-905.

Document 3: Allgaier, J. et al., Macromolecules 2007, 40 (3), 518-525.

Document 4: Malik, M. I. et al., Eur Polym J 2009, 45 (3), 899-910.

Step b)

The step b) is a step of introducing an ionizable group that ionizes in water or an aqueous solution into each of the linear molecules to provide first linear molecules.

In this step, for example, a carboxylic acid may be introduced as the ionizable group through an oxidation reaction using hypochlorous acid and 2,2,6,6-tetramethylpiperidine 1-oxyl.

In addition, in this step, for example, an amino group may be introduced through a coupling reaction using 1'-carbonyldiimidazole and ethylenediamine.

Further, in this step, for example, a sulfo group may be introduced through a reaction with 1,3-propane sultone.

It is desirable that the ionizable group be introduced so that each linear molecule may "have" the ionizable group wherever in the linear molecule the ionizable group is as long as the ionizable group contributes to the formation of the isolated nanosheet as described above, and it is desirable that the ionizable group be introduced so that the first linear molecules may each have the ionizable group preferably at or near at least one end thereof, more preferably at least one end thereof, still more preferably at or near each of both ends thereof, most preferably at each of both ends thereof.

Step c)

The step c) is a step of preparing the first cyclic molecules.

In this step, the cyclic molecules may be purchased on the market, or may be produced. When a derivative is to be prepared, the derivative may be obtained by, for example, a method described in Document 5: Khan, A. R. et al., Chem Rev 1998, 98 (5), 1977-1996 or the like.

The step c) only needs to be provided before the step d). That is, the step c) does not need to be provided after the step b), and may be performed separately from the steps a) and b).

Step d)

The step d) is a step of mixing the first linear molecules and the first cyclic molecules in water or an aqueous solution.

The water or the aqueous solution is not particularly limited as long as the water or the aqueous solution serves as a solvent capable of dissolving at least one of the cyclic molecules or the linear molecules.

Specific examples of the water or the aqueous solution to be used in the step d) may include, but not limited to, pure water, an aqueous solution of an alcohol, an aqueous solution of an acid, an aqueous solution of an alkali, a buffer, a culture medium, and blood plasma.

The above-mentioned isolated nanosheet can be obtained by the production method including the steps a) to d).

The above-mentioned production method may include a step other than the steps a) to d).

Examples of the step other than the steps a) to d) may include, but not limited to: a step of preparing the above-mentioned "linear molecules" "each including at least two moieties," which is provided before the step a); a step of purifying the isolated nanosheet, which is provided after the step d); and the inclusion of the cyclic molecules and the first substance and the synthesis of pseudo-polyrotaxanes or polyrotaxanes, which may be provided before the step a).

In addition, when the isolated nanosheet includes the above-mentioned second cyclic molecule, first substance, and second substance, the production method of the present invention may include a step for introducing the second cyclic molecule, the first substance, and the second substance into the isolated nanosheet.

Further, it is desirable to further include, after the step d), e) a step of modifying part of the pseudo-polyrotaxanes of the obtained isolated nanosheet.

The modifying step may be a step of introducing a first substituent into each of the first linear molecules, for example, at an end of each of the first linear molecules. As long as the isolated nanosheet is obtained, the first substituent may be a capping group having such a capping action as to prevent dissociation of the first cyclic molecules, may be a group having the action of an ionizable group, or may have any other action. The first substituent may have any combination of those actions, and may exhibit all the actions. For example, a group derived from folic acid, biotin, fluorescein, an oligopeptide, such as RGD or GRGDS, or a monoclonal antibody, such as rituximab, bevacizumab, tocilizumab, or infliximab, may be introduced as a group having the capping action and having the action of an ionizable group. For example, when a group derived from folic acid is to be introduced, the introduction may be performed by subjecting the isolated sheet to be obtained and folic acid to a reaction in the presence of a condensing agent, such as 4-(4,6-dimethoxy-1,3,5-triazin-2-yl)-4-methylmo/pholinium chloride (DMT/MM), N,N'-dicyclohexylcarbodiimide (DCC), 1-(3-dimethylaminopropyl)-3-ethylcarbodiimide (EDC), benzotriazol-1-yloxy-trisdimethylaminophosphonium salt (BOP), (benzotriazol-1-yloxy)tripyrrolizidinophosphonium hexafluorophosphate (PyBOP), or O-(7-azabenzotriazol-1-yl)-N,N,N',N'-tetramethyluronium hexafluorophosphate quvan.

The modifying step may be a step of introducing a second substituent into each of the first cyclic molecules as long as the isolated nanosheet is obtained.

Production Method II

The isolated nanosheet, including a plurality of pseudo-polyrotaxanes and/or polyrotaxanes, of the present application may be obtained by the following production method. That is, the isolated nanosheet can be obtained by the production method including the steps of:
  a) preparing the linear molecules;
  c) preparing the first cyclic molecules;
  d') mixing the linear molecules and the first cyclic molecules in water or an aqueous solution to obtain pseudo-polyrotaxanes and/or polyrotaxanes;
  b') introducing an ionizable group that ionizes in water or an aqueous solution into each of the linear molecules of the pseudo-polyrotaxanes and/or the polyrotaxanes obtained in the step d') to provide first linear molecules; and
  f) mixing the resultant pseudo-polyrotaxanes and/or polyrotaxanes in water or an aqueous solution.

The "step a)" and the "step c)" are the same steps that are described above.

In addition, the step d') is a step similar to the step d) described above. However, there is a difference in that, in the step d'), pseudo-polyrotaxanes and/or polyrotaxanes are obtained.

The step b') is a step similar to the step b) described above. However, there is a difference in that, while the step b') is a step to be performed after the formation of the pseudo-polyrotaxanes and/or the polyrotaxanes, the step b) is performed before the formation of the pseudo-polyrotaxanes or the isolated nanosheet.

The above-mentioned production method may include a step other than the steps a), c), d'), b'), and f).

Examples of the step other than the above-mentioned steps may include, but not limited to, the steps described in the foregoing.

As described above, the isolated nanosheet of the present invention can be formed in a self-organizing manner through the mixing step that is the step d) of the production method I or the mixing step that is the step f) of the production method II. Accordingly, the isolated nanosheet has a feature in that the isolated nanosheet not only is degraded when the conditions of a solution are changed, but also is regenerated when returned to the original conditions again.

It is conceived that the isolated nanosheet of the present invention is generated through the following action, which is, however, not based on a complete theory.

Figure 2:
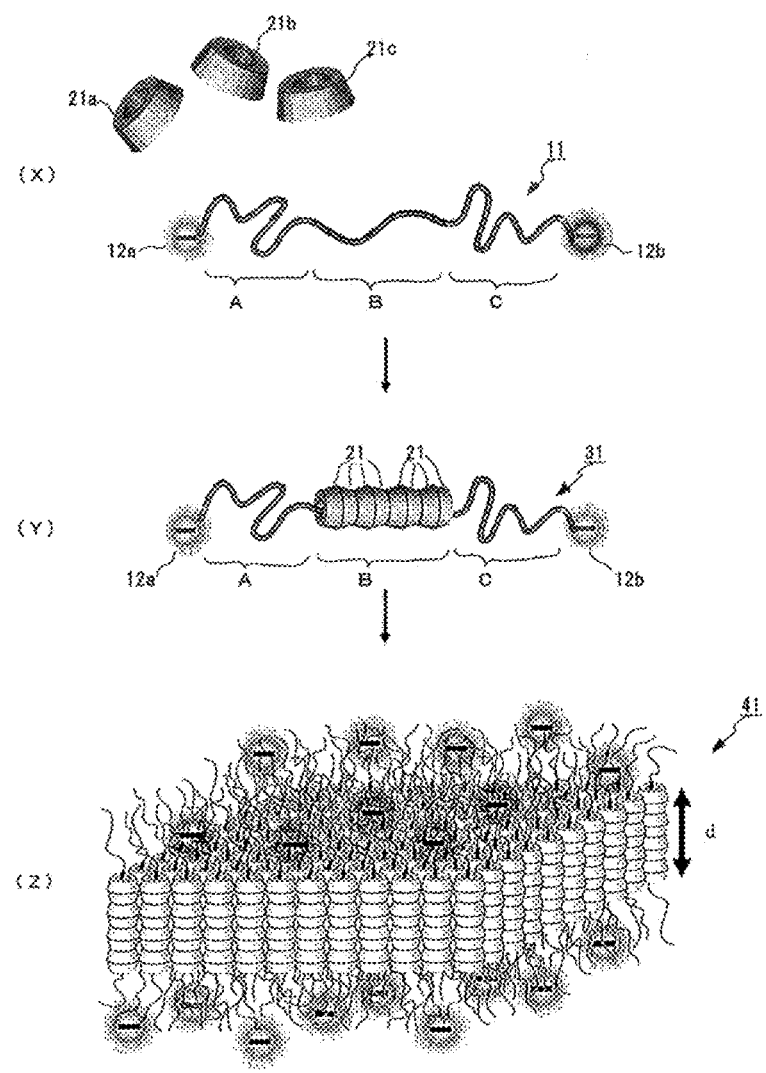
FIG. 2 is a schematic view for illustrating that, from (X) a triblock copolymer 11 and cyclic molecules 21, (Y) a pseudo-polyrotaxane 31 is formed, and (Z) an isolated nanosheet 41 of the present invention is formed through aggregation of a plurality of the pseudo-polyrotaxanes 31.

The action is described with reference to FIG. 2. FIG. 2 is a schematic view for illustrating that, from (X) a triblock copolymer 11 including blocks A, B, and C and cyclodextrin (CD) 21 serving as cyclic molecules, (Y) a pseudo-polyrotaxane 31 is formed, and (Z) an isolated nanosheet 41 of the present invention is formed through aggregation of a plurality of the pseudo-polyrotaxanes 31.

As described above, from (X) the triblock copolymer 11 including the blocks A, B, and C and including ionizable groups 12a and 12b at ends thereof, and the CD 21 serving as cyclic molecules, (Y) the pseudo-polyrotaxane 31 is formed. At this time, though depending on the properties of the blocks A to C, in (Y) of FIG. 2, it is illustrated that the CD 21 is aggregated on the central block B. In addition, the aggregation of the CD 21 on the central block B is also disclosed in Document 6: Fujita, H. et al., Macromol Chem Physic 1999, 200 (4), 706-713.

In the pseudo-polyrotaxane 31 obtained in (Y) of FIG. 2, the CD 21 present at the central portion thereof aggregates in a rod shape to form a column and become hydrophobic. Accordingly, as illustrated in (Z) of FIG. 2, the plurality of the pseudo-polyrotaxanes 31 assemble with each other in a self-organizing manner via the hydrophobic CD 21 forming a column, to thereby form the planar structure (nanosheet) 41. In (X) and (Y) of FIG. 2, the lengthwise direction of the triblock copolymer 11, i.e., a direction extending from the ionizable group 12a to the ionizable group 12b is illustrated as a horizontal direction, but in (Z) of FIG. 2, the lengthwise direction of the triblock copolymer 11 is illustrated as a vertical direction.

In the planar structure (nanosheet) 41 of (Z) of FIG. 2, ends of pseudo-polyrotaxane molecules of the present invention are ionized by having the ionizable groups 12a and 12b. Accordingly, the nanosheets do not adhere to or aggregate with each other in an aqueous solution, and hence the isolated nanosheets can be simply synthesized. A thickness d of the isolated nanosheet 41 is nearly equal to the length of the CD 21 forming a column, and hence can be easily controlled by changing the length of the central portion of the triblock copolymer 11.

There are many reported cases in which rod-shaped columns of cyclic molecules further aggregate with each other (for example, WO 2005/080470 A1). There are reports that, at the time of such aggregation, the rod-shaped columns aggregate while incorporating other cyclic molecules (corresponding to the above-mentioned first substance) or molecules (corresponding to the above-mentioned second substance) (Document 7: Liu, N.; Higashi et al., Int J Pharm 2017, 531 (2), 543-549.; and Document 8: Higashi, T. et al., Chem Pharm Bull (Tokyo) 2018, 66 (3), 207-216.)

Similarly, also in the case of the isolated nanosheet of the present invention, the first substance or the second substance may be incorporated into the nanosheet. When the conditions of a solution are changed to degrade the nanosheet, the first substance or the second substance is released into the solution. When the first substance and/or the second substance is a drug, the nanosheet can be utilized as a sustained-release or stimulus-responsive material for the drug.

EXAMPLES

Now, the present invention is described in more detail by way of Examples, but the present invention is by no means limited to the following Examples.

Synthesis Example 1: Synthesis of α, ω-Bis-Carboxylated Polyethylene Glycol-Block-Polypropylene Glycol-Block-Polyethylene Glycol α, ω-Bis-hydroxy polyethylene glycol-block-polypropylene glycol-block-polyethylene glycol (Pluronic (trademark) F68; $PEO_{76}PPO_{29}PEO_{76}$, $M_w$=8,400 g/mol; 2.50 g, 0.30 mmol), 2,2,6,6-tetramethylpiperidine 1-oxyl (TEMPO; 203 mg, 1.30 mmol), and sodium bromide NaBr (202 mg, 1.96 mmol) were dissolved in 28 mL of water. After that, while the solution was stirred, a 5 wt % aqueous solution of sodium hypochlorite was slowly added dropwise until the pH value ceased to change. The resultant aqueous solution was further stirred at room temperature for 10 minutes. After that, 2.5 mL of ethanol was put into the solution to quench the reaction. Further, a 6 M aqueous solution of hydrochloric acid was put into the solution until the pH reached 2, and the target product was extracted with 40 mL of methylene chloride. Further, the resultant methylene chloride solution was washed twice with a 0.01 M aqueous solution of hydrochloric acid, and then methylene chloride was evaporated to afford the target product (2.31 g, 0.275 mmol, 92.4%, Mn=5.7 kg/mol (polyethylene glycol standard in $CHCl_3$), PDI (polydispersity)=1.07).

Synthesis Example 2: Synthesis of α, ω-Bis-Amino Polyethylene Glycol-Block-Polypropylene Glycol-Block-Polyethylene Glycol A solution of α, ω-bis-hydroxy polyethylene glycol-block-polypropylene glycol-block-polyethylene glycol (Pluronic (trademark) F68; $PEO_{76}PPO_{29}PEO_{76}$, $M_w$=8,400 g/mol; 1 g, 0.119 mmol) in 10 mL of tetrahydrofuran was prepared, and added dropwise to a separately procured solution of 0.212 g (1.31 mmol) of 1,1'-carbonyldiimidazole in 6.3 mL of tetrahydrofuran. The resultant solution was further stirred at room temperature overnight, and then added dropwise to ethylenediamine (794 μL, 11.9 mmol). After the completion of the reaction, tetrahydrofuran was evaporated, and the resultant white solid was dissolved in water and then purified by dialysis. After the purification, water was removed by freeze-drying to afford the target product (0.92 g, 92%).

Synthesis Example 3: Synthesis of α, ω-Bis-Carboxylated Polyethylene Glycol 10 g of α, ω-bis-hydroxy polyethylene glycol was dissolved in 100 mL of water, and 2,2,6,6-tetramethylpiperidine 1-oxyl (TEMPO; 100 mg, 0.64 mmol) and sodium bromide (100 mg, 0.97 mmol) were put into the solution. After that, while the solution was stirred, a 5 wt % sodium hypochlorite aqueous solution was slowly added dropwise until the pH reached a value of from 10 to 11, followed by stirring at room temperature for 15 minutes. 10 mL of ethanol was put into the solution, and the pH of the solution was adjusted to 2 or less with a dilute hydrochloric acid solution to quench the reaction, followed by extraction with methylene chloride. Methylene chloride was evaporated under reduced pressure, followed by recrystallization from 250 mL of ethanol to afford the target product with a yield of 99% or more.

Synthesis Example 4: Synthesis of Polyrotaxanes P1 Having α, ω-Bis-Amino Polyethylene Glycol-Block-Polypropylene Glycol-Block-Polyethylene Glycol as Linear Molecule, β-CD as Cyclic Molecule, and Folic Acid at Both Ends 0.1 g of α, ω-bis-amino polyethylene glycol-block-polypropylene glycol-block-polyethylene glycol and 0.45 g of β-CD were mixed in 25 mL of water, and mixed for 1 week. The resulting precipitate was collected by centrifugation, and freeze-dried to afford 0.4 g of pseudo-polyrotaxanes as a powdery solid. The resultant pseudo-polyrotaxanes were dissolved in 5 mL of N,N-dimethylformamide, and then, to this solution, 0.27 g of benzotriazol-1-yloxy-trisdimethyl-aminophosphonium salt, 112 μL of N,N-diisopropylethyl-amine, and 0.14 g of folic acid were added, and the mixture was allowed to react overnight to afford polyrotaxanes P1 modified with folic acid. The isolation of the polyrotaxanes and the presence of folic acid were recognized by gel permeation chromatography and a proton nuclear magnetic resonance method.

Example 1: Preparation of Isolated Nanosheets X1 Using α, ω-Bis-Carboxylated Polyethylene Glycol-Block-Polypropylene Glycol-Block-Polyethylene Glycol and β-Cyclodextrin First, 0.45 g of β-cyclodextrin was dissolved in 25 mL of water.

Next, 0.1 g of α, ω-bis-carboxylated polyethylene glycol-block-polypropylene glycol-block-polyethylene glycol obtained in Synthesis Example 1 was put into the previously prepared aqueous solution of β-cyclodextrin, and the whole was stirred at room temperature for one week to afford target isolated nanosheets X1.

Figure 3:
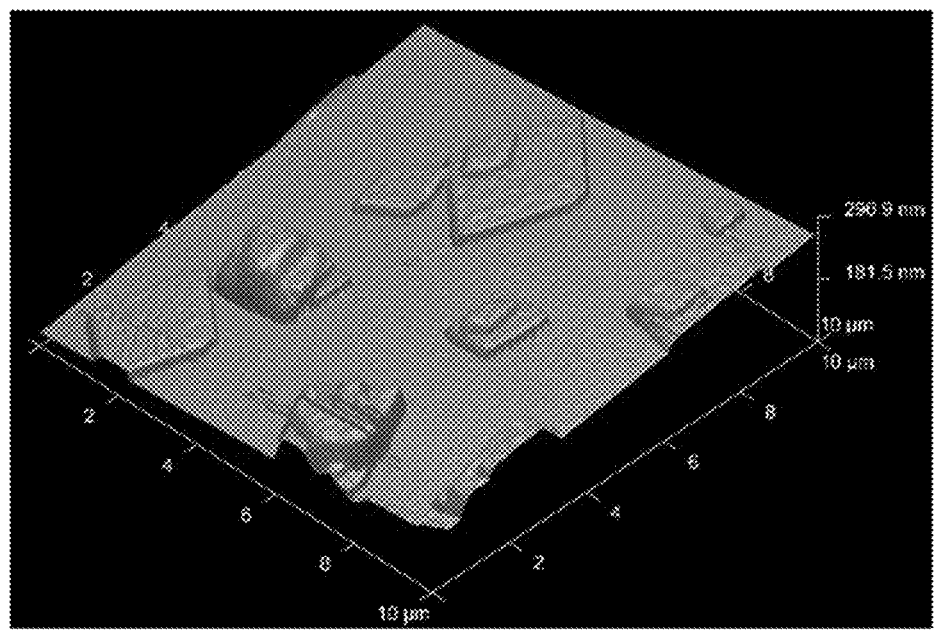
FIG. 3 shows an atomic force micrograph of isolated nanosheets X1 obtained in Example 1.
Figure 4:
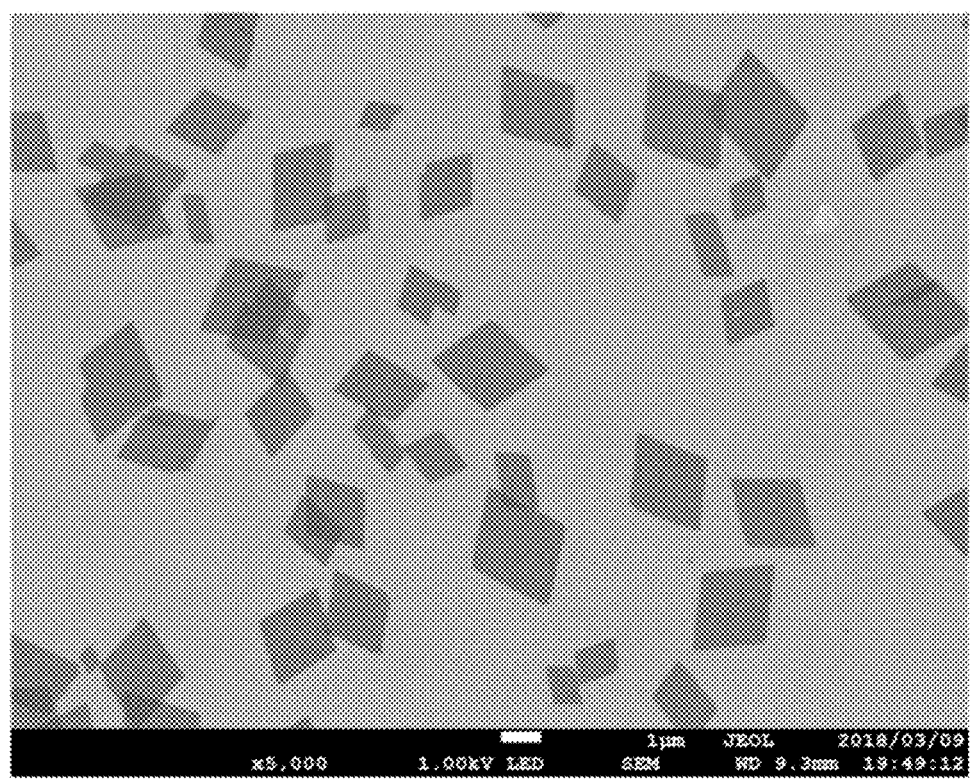
FIG. 4 shows a scanning electron micrograph of the isolated nanosheets X1 obtained in Example 1 (the white line represents 1 μm).

The formation of isolated nanosheets was recognized through small-angle X-ray scattering measurement, phase-contrast optical microscope observation, atomic force microscope observation (FIG. 3), and scanning electron microscope observation (FIG. 4).

It was found from the small-angle X-ray scattering measurement that the thickness of the β-cyclodextrin crystal portion of the isolated nanosheets X1 was 11 nm. In addition, it was recognized from the atomic force microscope observation that the thickness of the isolated nanosheets X1 including the polyethylene glycol moiety of the nanosheets was 15 nm, and it was recognized with a scanning microscope (or a phase-contrast microscope) that rhombic nanosheets measuring from 0.3 μm to 2 μm on each side were formed.

Grazing-incidence wide-angle X-ray diffraction (GI-WAXD) measurement of the isolated nanosheets X1 revealed that cyclodextrin (CD) was aligned in the isolated nanosheets (FIG. 4). When conversion into a 1D profile was performed through circular averaging, peaks were observed at the positions of 5.9°, 7.2°, 11.9°, 14.6°, 15.7°, 17.7°, and 19.1°. This indicates that CD formed a monoclinic crystal structure of a=1.910 nm, b=2.426 nm, c=1.568 nm, $\alpha=\gamma=90°$, and $\beta=111°$. Further, the angle of the rhombic structure was 74°, which agrees with an angle formed by a 110 plane and a "1"10 plane (where "1" represents a character with a bar above 1). That is, it may be concluded that the shape of the isolated nanosheets X1 reflects the monocrystalline structure.

The inclusion ratio of the isolated nanosheets X1 was 16.5%, and the thickness of the nanosheets was 11 nm.

Example 2: Preparation of Isolated Nanosheets X2 Using α, ω-Bis-Amino Polyethylene Glycol-Block-Polypropylene Glycol-Block-Polyethylene Glycol and β-Cyclodextrin First, 0.45 g of β-cyclodextrin was dissolved in 25 mL of water.

Next, 0.1 g of α, ω-bis-amino polyethylene glycol-block-polypropylene glycol-block-polyethylene glycol obtained in Synthesis Example 2 was put into the previously prepared aqueous solution of β-cyclodextrin, and the whole was stirred at room temperature for one week to afford target isolated nanosheets X2.

As in Example 1, the formation of isolated nanosheets was recognized through small-angle X-ray scattering measurement, phase-contrast optical microscope observation, atomic force microscope observation, and scanning electron microscope observation.

The inclusion ratio of the isolated nanosheets X2 was 16.5%, and the thickness of the nanosheets was 11 nm.

Example 3: Preparation of Isolated Nanosheets X3 Using α, ω-Bis-Carboxylated Polyethylene Glycol and α-Cyclodextrin First, 4.04 g of α-cyclodextrin was dissolved in 16.6 mL of water.

Next, 0.1 g of α, ω-bis-carboxylated polyethylene glycol obtained in Synthesis Example 3 was dissolved in 16.6 mL of water. Those aqueous solutions were mixed, and the mixture was stirred at room temperature for one week to afford target isolated nanosheets X3.

As in Example 1, the formation of isolated nanosheets was recognized through small-angle X-ray scattering measurement, phase-contrast optical microscope observation, atomic force microscope observation, and scanning electron microscope observation.

The inclusion ratio of the isolated nanosheets X3 was 95%, and the thickness of the nanosheets was 15 nm.

Example 4: Preparation of Isolated Nanosheets X4 Using α, ω-Bis-Carboxylated Polyethylene Glycol-Block-Polypropylene Glycol-Block-Polyethylene Glycol and γ-Cyclodextrin First, 4.04 g of γ-cyclodextrin was dissolved in 33 mL of water.

Next, 0.1 g of α, ω-bis-carboxylated polyethylene glycol-block-polypropylene glycol-block-polyethylene glycol obtained in Synthesis Example 1 was put into the previously prepared aqueous solution of γ-cyclodextrin, and the whole was stirred at room temperature for one week to afford target isolated nanosheets X4.

As in Example 1, the formation of isolated nanosheets was recognized through small-angle X-ray scattering measurement, phase-contrast optical microscope observation, atomic force microscope observation, and scanning electron microscope observation.

The inclusion ratio of the isolated nanosheets X4 was 22%, and the thickness of the nanosheets was 31 nm.

Example 5: Preparation of Isolated Nanosheets X5 Using α, ω-Bis-Carboxylated Polyethylene Glycol-Block-Polypropylene Glycol-Block-Polyethylene Glycol, β-Cyclodextrin, and Rhodamine (First Substance)

First, 0.45 g of β-cyclodextrin was dissolved in 25 mL of water. Further, 0.01 g of rhodamine and 0.1 g of α, ω-bis-carboxylated polyethylene glycol-block-polypropylene glycol-block-polyethylene glycol obtained in Synthesis Example 1 were put into the solution, and the whole was stirred at room temperature for one week to afford target isolated nanosheets X5 having rhodamine (first substance) incorporated therein.

Through observation of the fluorescence of the isolated nanosheets X5 in water with a fluorescence microscope, it was recognized that the first substance had been incorporated into the nanosheets.

Example 6: Preparation of Isolated Nanosheets X6 Using α, ω-Bis-Carboxylated Polyethylene Glycol-Block-Polypropylene Glycol-Block-Polyethylene Glycol, β-Cyclodextrin, and Lead Sulfide Quantum Nanodots (Second Substance)

First, 0.45 g of β-cyclodextrin was dissolved in 25 mL of water. Further, 0.01 g of lead sulfide quantum nanodots and 0.1 g of α, ω-bis-carboxylated polyethylene glycol-block-polypropylene glycol-block-polyethylene glycol obtained in Synthesis Example 1 were put into the solution, and the whole was stirred at room temperature for one week to afford target isolated nanosheets X6 having lead sulfide quantum nanodots (second substance) incorporated therein.

Through observation of the fluorescence of the isolated nanosheets X6 in water with a fluorescence microscope, it was recognized that the second substance had been incorporated into the nanosheets.

Example 7: Folic Acid Modification of Ends of Linear Molecules of Isolated Nanosheets X2

First, 0.14 g of folic acid, 92 mg of 4-(4,6-dimethoxy-1,3,5-triazin-2-yl)-4-methylmorpholinium chloride, and 34 μL of N-methylmorpholine were put into 10 mL of a 2 wt % water dispersion of the isolated nanosheets X2 obtained in Example 2, followed by mixing at room temperature overnight to afford folic acid-modified nanosheets X7. The nanosheets were purified by centrifugation, and then it was recognized from UV absorption spectrum measurement that the nanosheets were modified with folic acid.

Example 8: Production of Isolated Nanosheet X8 Using Polyrotaxanes P1

First, the polyrotaxanes P1 (0.5 g) obtained in Synthesis Example 4 were dissolved in 5 mL of N,N-dimethylformamide. The solution was added dropwise to 50 mL of a saturated aqueous solution of β-CD to afford isolated nanosheets X8.

As in Example 1, the formation of isolated nanosheets was recognized through small-angle X-ray scattering measurement, phase-contrast optical microscope observation, atomic force microscope observation, and scanning electron microscope observation.

The inclusion ratio of the isolated nanosheets X8 was 16.5%, and the thickness of the nanosheets was 11 nm.

Comparative Example 1: Preparation of Nanosheets Using α, ω-Bis-Hydroxy Polyethylene Glycol-Block-Polypropylene Glycol-Block-Polyethylene Glycol and β-Cyclodextrin First, 0.45 g of β-cyclodextrin was dissolved in 25 mL of water.

Figure 5:
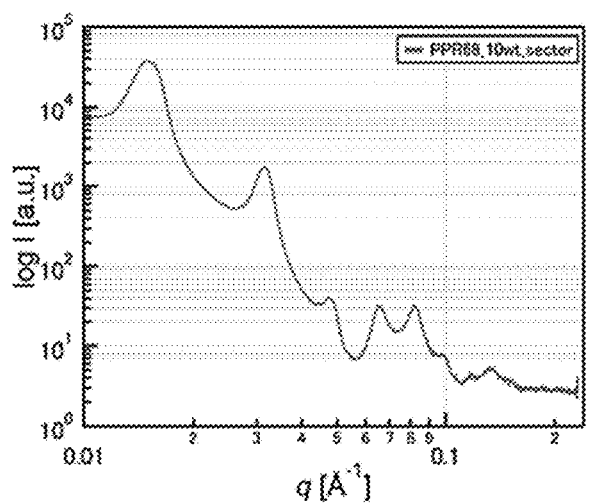
FIG. 5 is a graph showing the results of small-angle X-ray scattering measurement of aggregated nanosheets CX1 of Comparative Example 1.
Figure 6:
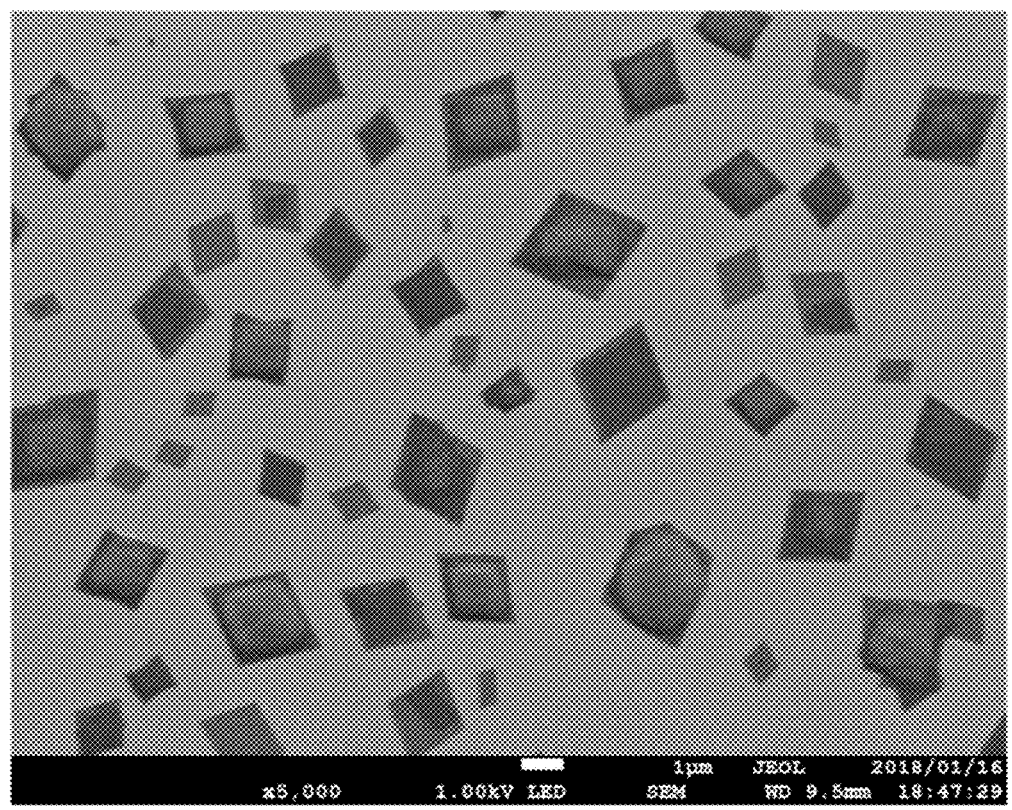
FIG. 6 shows a scanning electron micrograph of the aggregated nanosheets CX1 of Comparative Example 1 (the white line represents 1 μm).

Next, 0.1 g of α, ω-bis-hydroxy polyethylene glycol-block-polypropylene glycol-block-polyethylene glycol was put into the previously prepared aqueous solution of β-cyclodextrin, and the whole was stirred at room temperature for one week to afford aggregated nanosheets CX1.

α, ω-Bis-hydroxy polyethylene glycol-block-polypropylene glycol-block-polyethylene glycol has hydroxy groups as end functional groups of its linear molecules, and has a pKa value of about 16 under a neutral condition, and hence most of the hydroxy groups are not dissociated. Therefore, when nanosheets are produced Using the linear molecules, the nanosheets adhere to and aggregate with each other through an intermolecular interaction. It was recognized that the nanosheets aggregated with each other from: the fact that a lamellar structure factor was observed through small-angle X-ray scattering measurement (FIG. 5); and a state in which the nanosheets adhered to and aggregated with each other in scanning electron microscope observation (FIG. 6).

Example 9: Preparation of Isolated Nanosheets X1 Using α, ω-Bis-Carboxylated Polyethylene Glycol-Block-Polypropylene Glycol-Block-Polyethylene Glycol and β-Cyclodextrin, and Test for Degradation and Reconstruction of Nanosheets Through pH Adjustment A solution A-1 containing the target isolated nanosheets X1 was obtained in the same manner as in Example 1.

Figure 7:
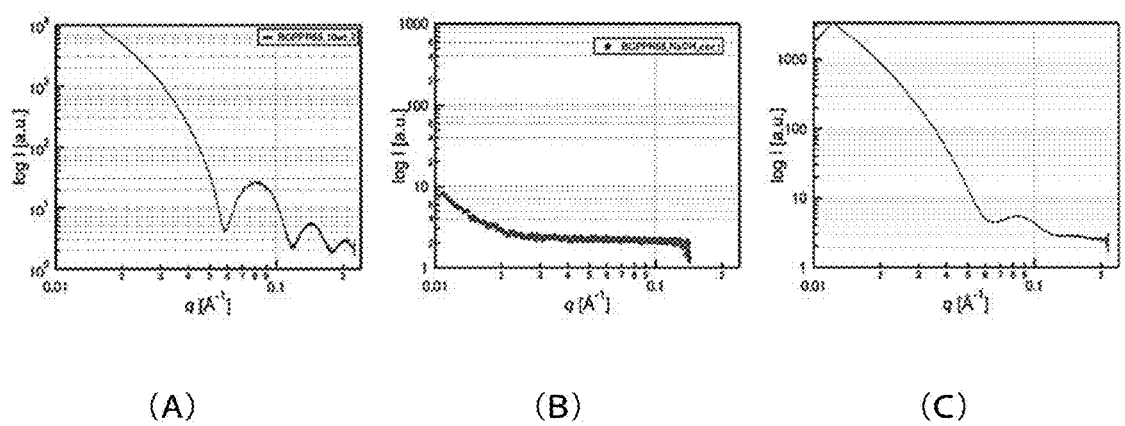
FIG. 7 are graphs showing the results of small-angle X-ray scattering measurement of the isolated nanosheets X1 of Example 1 and Example 6.

A shape factor for a sheet structure was observed in small-angle X-ray scattering measurement, and thus the formation of isolated nanosheets was recognized (FIG. 7(A)).

Next, sodium hydroxide was put into the solution A-1 until the pH reached 11 to give a solution A-2, followed by small-angle X-ray scattering measurement. As a result, it was found that the shape factor for a sheet structure had disappeared (FIG. 7(B)).

It was found from the above-mentioned results that, along with an increase in pH, a repulsive interaction acts between β-cyclodextrin molecules in the isolated nanosheets to disintegrate the isolated nanosheets.

Further, acetic acid was put into the solution A-2 to adjust the pH to 7 to give a solution A-3, followed by small-angle X-ray scattering measurement. As a result, the reconstruction of a sheet structure was recognized (FIG. 7(C)).

The above-mentioned results revealed that the isolated nanosheets repeated structure formation and disintegration through pH adjustment.

Example 10: Preparation of Drug-introduced Isolated Nanosheets X10 Using α, ω-Bis-Hydroxy Polyethylene Glycol-Block-Polypropylene Glycol-Block-Polyethylene Glycol, β-Cyclodextrin, and Naproxen First, 18 mg of β-cyclodextrin was dissolved in 1 mL of water. Next, 0.3 mg of naproxen was put into the aqueous solution of β-cyclodextrin, and the whole was stirred to complete dissolution in the water. Subsequently, 4 mg of α, ω-bis-hydroxy polyethylene glycol-block-polypropylene glycol-block-polyethylene glycol (Pluronic (trademark) F68; $PEO_{76}PPO_{29}PEO_{76}$, $M_w$=8,400 g/mol) was put into the previously prepared aqueous solution of β-cyclodextrin and naproxen, and the whole was stirred at room temperature for two weeks to afford target isolated nanosheets X10.

Figure 8:
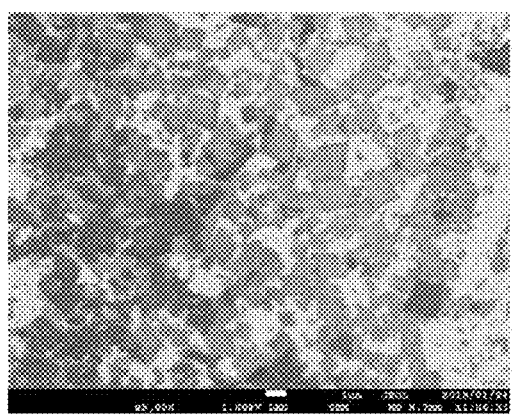
FIG. 8 shows a scanning electron micrograph of isolated nanosheets X10 of Example 10.

The resultant isolated nanosheets X10 were observed with a scanning electron microscope. As a result, it is found that nanosheets have been formed (FIG. 8).

Figure 9:
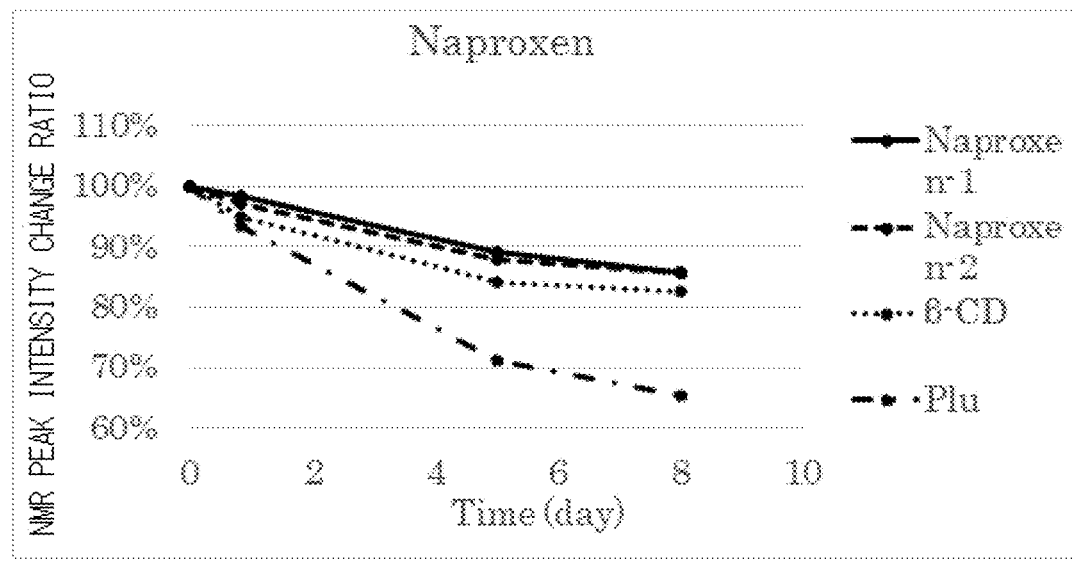
FIG. 9(a) and FIG. 9(b) are graphs showing changes in NMR peak intensity of each constituent component of the isolated nanosheets X10 of Example 10.
Figure 9:
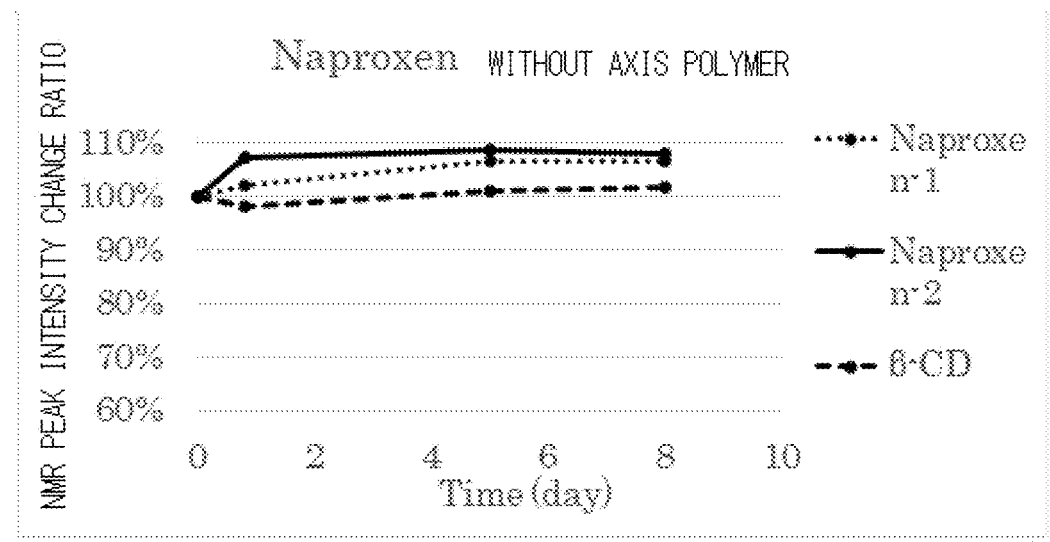

In addition, FIG. 9(a) and FIG. 9(b) are graphs showing changes in NMR peak intensity of each constituent component of the nanosheets. It is found from the graphs that nanosheets including naproxen have been formed (FIG. 9(a)), and that nanosheets including naproxen are not formed in the absence of Pluronic (axis molecule) (FIG. 9(b)).

Example 11: Preparation of Drug-Introduced Isolated Nanosheets X11 Using α, ω-Bis-Hydroxy Polyethylene Glycol-Block-Polypropylene Glycol-Block-Polyethylene Glycol, β-Cyclodextrin, and Prednisolone Acetate First, 18 mg of β-cyclodextrin was dissolved in 1 mL of water. Next, 0.53 mg of prednisolone acetate was put into the aqueous solution of β-cyclodextrin, and the whole was stirred to complete dissolution in the water. Subsequently, 4 mg of α, ω-bis-hydroxy polyethylene glycol-block-polypropylene glycol-block-polyethylene glycol (Pluronic (trademark) F68; $PEO_{76}PPO_{29}PEO_{76}$, $M_w$=8,400 g/mol) was put into the previously prepared aqueous solution of β-cyclodextrin and prednisolone acetate, and the whole was stirred at room temperature for two weeks to afford target isolated nanosheets X11.

Figure 10:
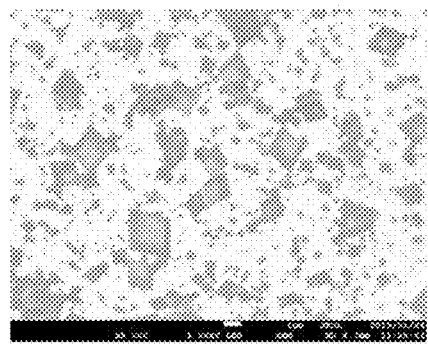
FIG. 10 shows a scanning electron micrograph of isolated nanosheets X11 of Example 11.

The resultant isolated nanosheets X11 were observed with a scanning electron microscope. As a result, it is found that nanosheets have been formed (FIG. 10).

Example 12: Preparation of Drug-introduced Isolated Nanosheets X12 Using α, ω-Bis-Hydroxy Polyethylene Glycol-Block-Polypropylene Glycol-Block-Polyethylene Glycol, γ-Cyclodextrin, and Rebamipide First, 50 mg of γ-cyclodextrin was dissolved in 1 mL of water. Next, 1.2 mg of rebamipide was put into the aqueous solution of γ-cyclodextrin, and the whole was stirred to complete dissolution in the water. Subsequently, 30 mg of α, ω-bis-hydroxy polyethylene glycol-block-polypropylene glycol-block-polyethylene glycol (Pluronic (trademark) F108; $PEO_{126}PPO_{56}PEO_{126}$, $M_w$=14,600 g/mol) was put into the previously prepared aqueous solution of γ-cyclodextrin and rebamipide, and the whole was stirred at room temperature for two weeks to afford target isolated nanosheets X12.

Figure 11:
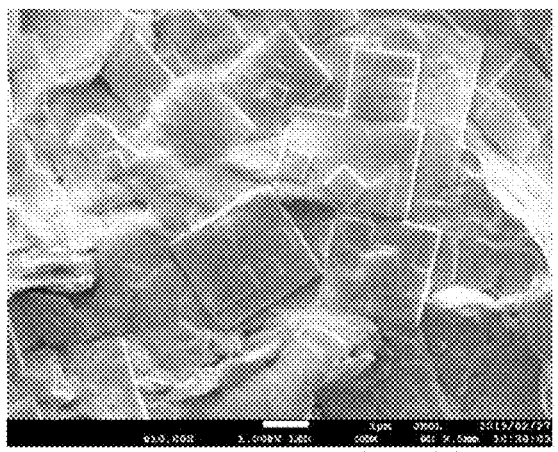
FIG. 11 shows a scanning electron micrograph of isolated nanosheets X12 of Example 12.

The resultant isolated nanosheets X12 were observed with a scanning electron microscope. As a result, it is found that nanosheets have been formed (FIG. 11).

Figure 12:
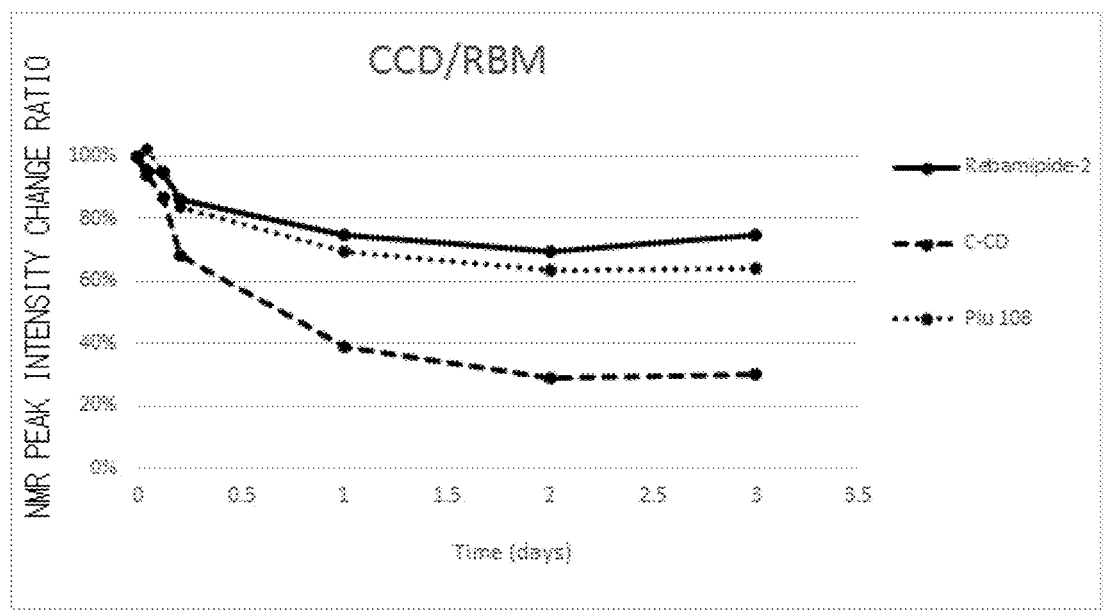
FIG. 12 is a graph showing changes in NMR peak intensity of each constituent component of the isolated nanosheets X12 of Example 12.

In addition, FIG. 12 is a graph showing changes in NMR peak intensity of each constituent component of the nanosheets. It is found from the graph that nanosheets including rebamipide have been formed.

Example 13: Preparation of Drug-Introduced Isolated Nanosheets X13 Using α, ω-Bis-Hydroxy Polyethylene Glycol-Block-Polypropylene Glycol-Block-Polyethylene Glycol, γ-Cyclodextrin, and Salbutamol Sulfate First, 50 mg of γ-cyclodextrin was dissolved in 1 mL of water. Next, 1.9 mg of salbutamol sulfate was put into the aqueous solution of γ-cyclodextrin, and the whole was stirred to complete dissolution in the water. Subsequently, 30 mg of α, ω-bis-hydroxy polyethylene glycol-block-polypropylene glycol-block-polyethylene glycol (Pluronic (trademark) F108; $PEO_{126}PPO_{56}PEO_{126}$, $M_w$=14,600 g/mol) was put into the previously prepared aqueous solution of γ-cyclodextrin and salbutamol sulfate, and the whole was stirred at room temperature for two weeks to afford target isolated nanosheets X13.

Figure 13:
FIG. 13 shows a scanning electron micrograph of isolated nanosheets X13 of Example 13.

The resultant isolated nanosheets X13 were observed with a scanning electron microscope. As a result, it is found that nanosheets have been formed (FIG. 13).

Example 14: Preparation of Drug-introduced Isolated Nanosheets X14 Using α, ω-Bis-Hydroxy Polyethylene Glycol-Block-Polypropylene Glycol-Block-Polyethylene Glycol, γ-Cyclodextrin, and Flurbiprofen First, 50 mg of γ-cyclodextrin was dissolved in 1 mL of water. Next, 0.78 mg of flurbiprofen was put into the aqueous solution of γ-cyclodextrin, and the whole was stirred to complete dissolution in the water. Subsequently, 30 mg of α, ω-bis-hydroxy polyethylene glycol-block-polypropylene glycol-block-polyethylene glycol (Pluronic (trademark) F108; $PEO_{126}PPO_{56}PEO_{126}$, $M_w$=14,600 g/mol) was put into the previously prepared aqueous solution of γ-cyclodextrin and flurbiprofen, and the whole was stirred at room temperature for two weeks to afford target isolated nanosheets X14.

Figure 14:
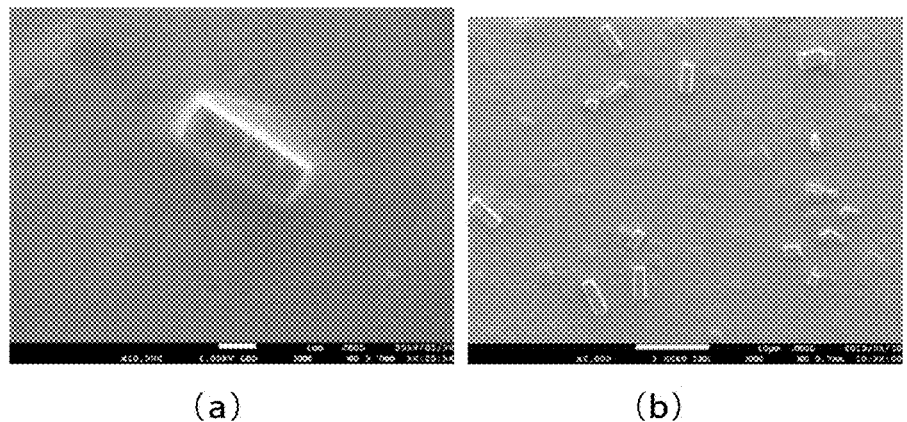
FIG. 14 show scanning electron micrographs of isolated nanosheets X14 of Example 14.

The resultant isolated nanosheets X14 were observed with a scanning electron microscope. As a result, it is found that nanosheets have been formed (FIG. 14).

Example 15: Preparation of Drug-Introduced Isolated Nanosheets X15 Using α, ω-Bis-Hydroxy Polyethylene Glycol-Block-Polypropylene Glycol-Block-Polyethylene Glycol, γ-Cyclodextrin, and Beclomethasone Dipropionate First, 50 mg of γ-cyclodextrin was dissolved in 1 mL of water. Next, 1.7 mg of beclomethasone dipropionate was put into the aqueous solution of γ-cyclodextrin, and the whole was stirred to complete dissolution in the water. Subsequently, 30 mg of α, ω-bis-hydroxy polyethylene glycol-block-polypropylene glycol-block-polyethylene glycol (Pluronic (trademark) F108; $PEO_{126}PPO_{56}PEO_{126}$, g/mol) was put into the previously prepared aqueous solution of γ-cyclodextrin and beclomethasone dipropionate, and the whole was stirred at room temperature for two weeks to afford target isolated nanosheets X15.

Figure 15:
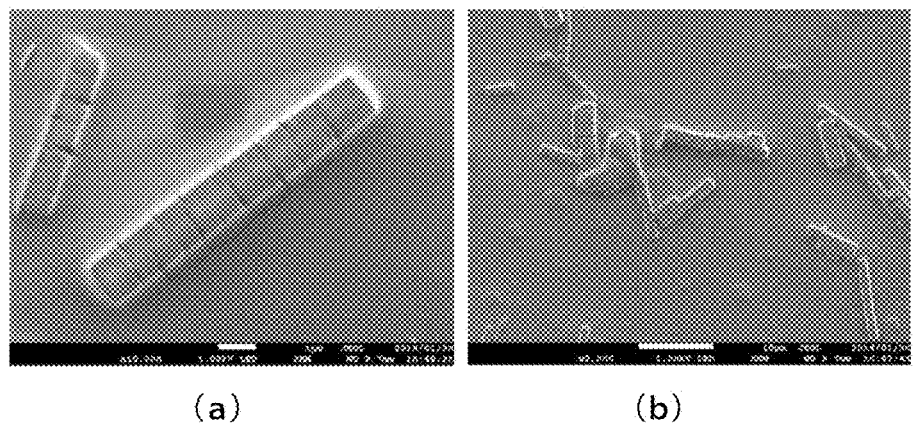
FIG. 15 show scanning electron micrographs of isolated nanosheets X15 of Example 15.

The resultant isolated nanosheets X15 were observed with a scanning electron microscope. As a result, it is found that nanosheets have been formed (FIG. 15).

Example 16: Preparation of Drug-Introduced Isolated Nanosheets X16 Using α, ω-Bis-Hydroxy Polyethylene Glycol-Block-Polypropylene Glycol-Block-Polyethylene Glycol, γ-Cyclodextrin, and Piroxicam First, 50 mg of γ-cyclodextrin was dissolved in 1 mL of water. Next, 1.1 mg of piroxicam was put into the aqueous solution of γ-cyclodextrin, and the whole was stirred to complete dissolution in the water. Subsequently, 30 mg of α, ω-bis-hydroxy polyethylene glycol-block-polypropylene glycol-block-polyethylene glycol (Pluronic (trademark) F108; $PEO_{126}PPO_{56}PEO_6$, $M_w$=14,600 g/mol) was put into the previously prepared aqueous solution of γ-cyclodextrin and piroxicam, and the whole was stirred at room temperature for two weeks to afford target isolated nanosheets X16.

Figure 16:
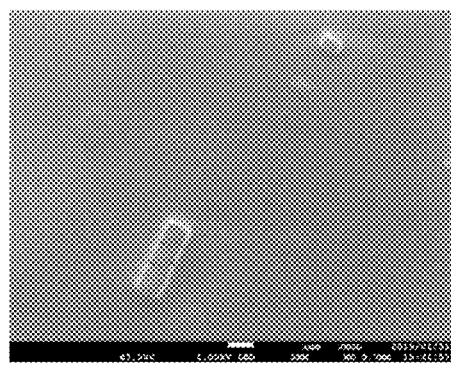
FIG. 16 shows a scanning electron micrograph of isolated nanosheets X16 of Example 16.

The resultant isolated nanosheets X16 were observed with a scanning electron microscope. As a result, it is found that nanosheets have been formed (FIG. 16).

Example 17: Preparation of Drug-introduced Isolated Nanosheets X17 Using α, ω-Bis-Hydroxy Polyethylene Glycol-Block-Polypropylene Glycol-Block-Polyethylene Glycol, γ-Cyclodextrin, and Ketoprofen First, 50 mg of γ-cyclodextrin was dissolved in 1 mL of water. Next, 0.82 mg of ketoprofen was put into the aqueous solution of γ-cyclodextrin, and the whole was stirred to complete dissolution in the water. Subsequently, 30 mg of α, ω-bis-hydroxy polyethylene glycol-block-polypropylene glycol-block-polyethylene glycol (Pluronic (trademark) F108; $PEO_{126}PPO_{56}PEO_{126}$, $M_w$=14,600 g/mol) was put into the previously prepared aqueous solution of γ-cyclodextrin and ketoprofen, and the whole was stirred at room temperature for two weeks to afford target isolated nanosheets X17.

Figure 17:
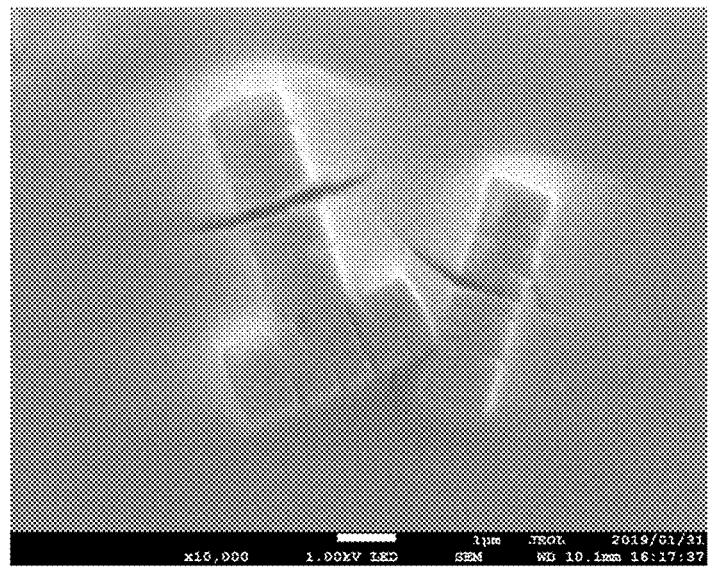
FIG. 17 shows a scanning electron micrograph of isolated nanosheets X17 of Example 17.

The resultant isolated nanosheets X17 were observed with a scanning electron microscope. As a result, it is found that nanosheets have been formed (FIG. 17).

Example 18: Preparation of Isolated Nanosheets X18 Using α, ω-Bis-Amino Polyethylene Glycol-Block-Polypropylene Glycol-Block-Polyethylene Glycol, β-Cyclodextrin, and Rhodamine (First Substance)

First, 0.45 g of β-cyclodextrin was dissolved in 25 mL of water. Further, 0.01 g of rhodamine and 0.1 g of α, ω-bis-amino polyethylene glycol-block-polypropylene glycol-block-polyethylene glycol obtained in Synthesis Example 2 were put into the solution, and the whole was stirred at room temperature for one week to afford target isolated nanosheets X18 having rhodamine (first substance) incorporated therein.

Figure 18:
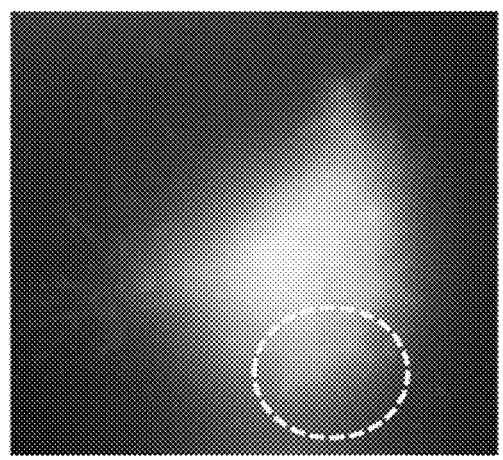
FIG. 18 shows a fluorescence microscope of isolated nanosheets X18 of Example 18.

Example 19: Observation of Adhesion Between HeLa Cells and Rhodamine-$NH_2$-Nanosheets with Fluorescence Microscope A glass bottom dish having HeLa cells settled in 2,000 μL of D10 medium was procured. The volume of the medium was adjusted to 1,750 µL by taking 250 µL thereof, and then 250 µL of the isolated nanosheets X18 having rhodamine (first substance) incorporated therein obtained by the method described above were added, followed by observation with a fluorescence microscope. As a result, a state in which the nanosheets were adhering to cell surfaces was observed (FIG. 18).

Example 20: Washing Experiment on Nanosheets Adhering to Cells

Figure 19:
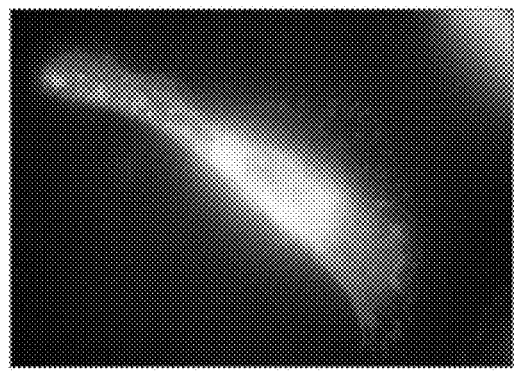
FIG. 19 show scanning electron micrographs of isolated nanosheets X18 of Example 18 before and after washing (FIG. 19(a): before washing.
Figure 19:
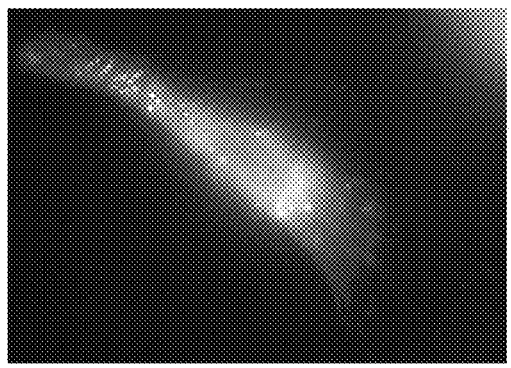
Figure 20:
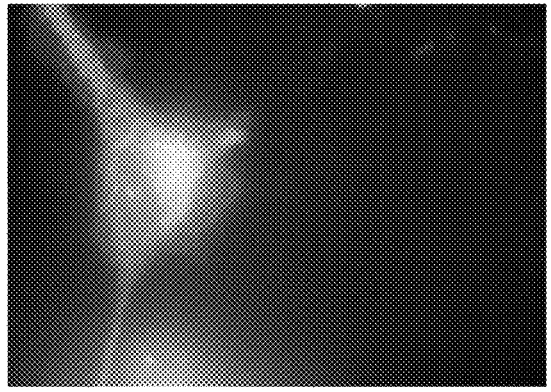
FIG. 20 shows a fluorescence microscope of isolated nanosheets X21 after 24 hours of incubation.
Figure 21:
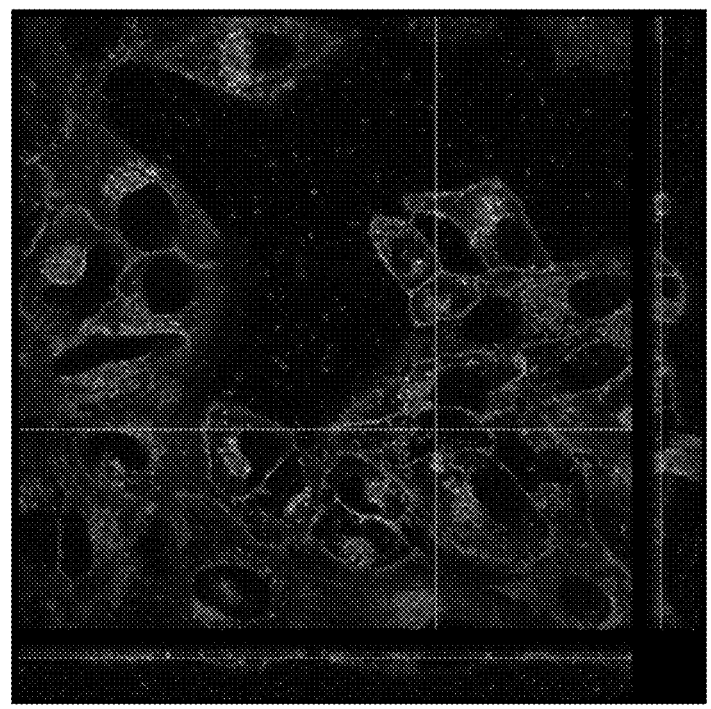
FIG. 21 shows a confocal laser fluorescence micrograph of isolated nanosheets X22 obtained in Example 23, which are adhering to cell surfaces.

The isolated nanosheets X18 having rhodamine (first substance) incorporated therein were caused to adhere to cell surfaces by the same method as in Example 19, and then the resultant was washed with D10 medium so that the nanosheet concentration became 1/512. However, the isolated nanosheets X having rhodamine (first substance) incorporated therein remained adhering to cell surfaces. FIG. 19(a) is a scanning electron micrograph taken before the washing, and FIG. 19(b) is a scanning electron micrograph taken after the washing. When the two micrographs are compared to each other, there is no marked difference, and hence it is found that the washing does not lead to a state in which rhodamine has been washed off and lost.

Example 21: Washing of Nanosheets Adhering to Cells, and Subsequent Degradation of Nanosheets Over 24 Hours Isolated nanosheets X21 having rhodamine (first substance) incorporated therein were caused to adhere to cell surfaces by the same methods as in Examples 19 and 20, and then the resultant was washed with D10 medium so that the nanosheet concentration became 1/512. However, the isolated nanosheets X21 having rhodamine (first substance) incorporated therein remained adhering to cell surfaces. After that, the cells were incubated in an incubator for 24 hours, and then the cells were observed with a fluorescence microscope again. As a result, no nanosheet structure was observed, and hence it was found that the nanosheets adhering to the cell surfaces were degraded over 24 hours.

Example 22: Preparation of Isolated Nanosheets X22 Having Fluorescent Molecules Bound to Ends of Part of Axis Molecules 1 mg of fluorescein isothiocyanate (FITC) was dissolved in 1 mL of pure water to prepare a solution of FITC. After that, 1 µL of the solution of FITC was taken and mixed with 1,000 µL of a previously prepared water dispersion of $NH_2$-nanosheets, and then the mixture was shaken at room temperature overnight to afford isolated nanosheets X22 having fluorescent molecules bound to ends of part of axis molecules.

Example 23: Observation of Adhesion Between HeLa Cells and FITC-$NH_2$-Nanosheet with Fluorescence Microscope A glass bottom dish having HeLa cells settled in 2,000 µL of D10 medium was procured, and cell membranes were stained with Cell Brite Red. The volume of the D10 medium was adjusted to 1,800 µL by taking 200 µL of the medium in the dish, and then 200 µL of a water dispersion of FITC-$NH_2$-nanosheets, which contained the isolated nanosheets X22 procured by the method of Example 22, was added. Medium exchange of a volume of 1,000 µL out of the volume of the glass bottom dish, i.e., 2,000 µL was repeated 4 times, followed by three-dimensional observation with a confocal laser fluorescence microscope. As a result, sites with high fluorescence intensities were observed on cell surfaces, revealing that the isolated nanosheets X22 were adhering to the cell surfaces.

The invention claimed is:
1. An isolated nanosheet comprising a plurality of pseudo-polyrotaxanes and/or polyrotaxanes each having one or more first cyclic molecules and one or more linear molecules included in a cavity of at least one of the one or more first cyclic molecules in a skewered manner,
   wherein the one or more linear molecules include, as part thereof, first linear molecules each having an ionizable group that ionizes in water or an aqueous solution,
   each of the first linear molecules is (i) a linear molecule including a linear polymer formed of only one type of repeating unit or (ii) a block copolymer including at least three blocks,
   when each of the first linear molecules is (i) the linear molecule including the linear polymer formed of only one type of repeating unit, the linear polymer includes polyethylene glycol (PEG) and at least one of the first cyclic molecules is a cyclodextrin,
   when each of the first linear molecules is (i) the linear molecule including a linear polymer formed of only one type of repeating unit, the inclusion ratio of the pseudo-polyrotaxanes and/or the polyrotaxanes is at least 95% when the specified inclusion ratio is set to 100%,
   when each of the first linear molecules is (ii) the block copolymer including at least three blocks, the block polymer includes PEO-PPO-PEO and at least one of the first cyclic molecules is a cyclodextrin, and
   when each of the first linear molecules is (ii) the block copolymer including at least three blocks, the inclusion ratio of the pseudo-polyrotaxanes and/or the polyrotaxanes is at least 10% when the specified inclusion ratio is set to 100%.

2. The isolated nanosheet according to claim 1, wherein the first linear molecules each have the ionizable group at or near at least one end thereof.

3. The isolated nanosheet according to claim 1, wherein the first linear molecules each have the ionizable group at or near each of both ends thereof.

4. The isolated nanosheet according to claim 1, wherein the ionizable group is at least one kind selected from the group consisting of a carboxyl group, an amino group, a sulfo group, a phosphoric acid group, a trimethylamine hydrochloride group, a trimethylamine hydrochloride group, a dimethylamino group, a diethylamino group, a methylamino group, an ethylamino group, a pyrrolidine group, a pyrrole group, an ethyleneimine group, a piperidine group, a pyridine group, a pyrylium ion group, a thiopyrylium ion group, a hexamethyleneimine group, an azide group, an imidazole group, a pyrazole group, an oxazole group, a thiazole group, an imidazoline group, a morpholine group, a thiazine group, a triazole group, a tetrazole group, a pyridazine group, a pyrimidine group, a pyrazine group, an indole group, a benzimidazole group, a purine group, a benzotriazole group, a quinoline group, a quinazoline group, a quinoxaline group, a pteridine group, a carbazole group, a porphyrin group, a chlorin group, a choline group, an adenine group, a guanine group, a cytosine group, a thymine group, a uracil group, a dissociated thiol group, a dissociated hydroxy group, an azido group, a pyridine group, a carbamic acid, a guanidine, a sulfenic acid, a urea, a thiourea, a peroxy acid, and analogs and derivatives thereof.

5. The isolated nanosheet according to claim 1, wherein each of the first linear molecules is (i) the linear molecule including the linear polymer formed of only one type of repeating unit, the linear polymer includes polyethylene glycol (PEG), and at least one of the first cyclic molecules is a cyclodextrin.

6. The isolated nanosheet according to claim 1, wherein each of the first linear molecules is (ii) the block copolymer including at least three blocks, the block polymer includes PEO-PPO-PEO, and at least one of the first cyclic molecules is a cyclodextrin.

7. The isolated nanosheet according to claim 1, further comprising a second cyclic molecule, wherein none of the one or more linear molecules are included in the second cyclic molecule in a skewered manner.

8. The isolated nanosheet according to claim 7, wherein the second cyclic molecule has a first substance included by a cavity thereof.

9. The isolated nanosheet according to claim 7, comprising at least two first cyclic molecules, wherein at least one of the first cyclic molecules is the cyclodextrin, and wherein the other one or more first cyclic molecules and the second cyclic molecule are each selected from the group consisting of α-cyclodextrin, β-cyclodextrin, γ-cyclodextrin, a crown ether, a pillararene, a calixarene, a cyclophane, a cucurbituril, and derivatives thereof.

10. The isolated nanosheet according to claim 1, further comprising a second substance.

11. The isolated nanosheet according to claim 1, wherein the one or more linear molecules are each a copolymer having a configuration represented by: "a moiety formed of polyethylene glycol (PEG)-a moiety formed of polypropylene glycol (PPG)-a moiety formed of PEG," and
wherein the one or more first cyclic molecules are each β-cyclodextrin.

12. The isolated nanosheet according to claim 1, wherein the one or more linear molecules are each a triblock copolymer formed only of a configuration represented by: "a moiety formed of polyethylene glycol (PEG)-a moiety formed of polypropylene glycol (PPG)-a moiety formed of PEG," and
wherein the one or more first cyclic molecules are each β-cyclodextrin.

13. The isolated nanosheet according to claim 1, wherein the isolated nanosheet has a thickness of from 0.5 nm to 100 nm.

14. The isolated nanosheet according to claim 1,
wherein the one or more linear molecules includes a moiety formed of polyethylene glycol (PEG) and/or a moiety formed of polypropylene glycol (PPG), and
wherein the one or more first cyclic molecules are each selected from the group consisting of α-cyclodextrin, β-cyclodextrin, γ-cyclodextrin, and derivatives thereof.

15. The isolated nanosheet according to claim 1,
wherein the one or more linear molecules include polyethylene glycol (PEG) and/or polypropylene glycol (PPG), and
wherein the one or more first cyclic molecules are each selected from the group consisting of α-cyclodextrin, β-cyclodextrin, γ-cyclodextrin, and derivatives thereof.

16. A material comprising the isolated nanosheet of claim 1.

17. A pharmaceutical carrier and/or a pharmaceutical vehicle comprising the isolated nanosheet of claim 1.

18. The pharmaceutical carrier and/or the pharmaceutical vehicle according to claim 17, wherein the isolated sheet is configured to adhere to a target site.

19. A pharmaceutical disintegrant and/or a pharmaceutical binder comprising the isolated nanosheet of claim 1.

20. A pharmaceutical comprising:
a pharmaceutically acceptable active ingredient; and
the isolated nanosheet of claim 1.

21. A pharmaceutical comprising:
a pharmaceutically acceptable active ingredient; and
a pharmaceutical carrier and/or a pharmaceutical vehicle including the isolated nanosheet of claim 1.

* * * * *